United States Patent
Kawabe et al.

(10) Patent No.: US 7,358,046 B2
(45) Date of Patent: Apr. 15, 2008

(54) SENSITIVITY TEST TO PREDICT EFFICACY OF ANTI-CANCER THERAPIES

(75) Inventors: Takumi Kawabe, Numazu (JP); Hidetaka Kobayashi, Numazu (JP)

(73) Assignee: Canbas Co., Ltd., Shizuoka (JP)

( * ) Notice: Subject to any disclaimer, the term of this patent is extended or adjusted under 35 U.S.C. 154(b) by 439 days.

(21) Appl. No.: 10/913,711

(22) Filed: Aug. 6, 2004

(65) Prior Publication Data

US 2006/0014157 A1 Jan. 19, 2006

Related U.S. Application Data

(60) Provisional application No. 60/494,022, filed on Aug. 8, 2003.

(51) Int. Cl.
C12Q 1/68 (2006.01)
G01N 33/574 (2006.01)
A01N 37/18 (2006.01)

(52) U.S. Cl. .................. 435/6; 435/7.23; 514/2

(58) Field of Classification Search .......... 435/6, 435/7.23; 514/2
See application file for complete search history.

(56) References Cited

U.S. PATENT DOCUMENTS

| 2004/0091947 A1* | 5/2004 | Broude et al. ............ 435/7.23 |
| 2004/0198727 A1 | 10/2004 | Kawabe et al. |
| 2004/0248783 A1 | 12/2004 | Kawabe et al. |

OTHER PUBLICATIONS

Suganuma et al. (Can. Res. 59:5887-5891 (1999).*
Koizumi et al. (Biochem. Biophys. Acta 1693:47-55 (2004)).*
Stedman's Medical Dictionary 27th Ed. (definition of "peptide" (pp. 1-2)).*
Black et al., "Further Observations on the Effects of Cancer Chemotherapeutic Agents on the in Vitro Dehydrogenase Activity of Cancer Tissue", *J. Nat. Cancer Inst.*, 1954; 14(5): 1147-1158.
Salmon et al., "Quantitation of Differential Sensitivity of Human-Tumor Stem Cells to Anticancer Drugs", *N. Engl. J. Med.*, 1978; 298(24): 1321-1327.
Hildebrand-Zanki et al., "In Vitro Assays for New Drug Screening: Comparison of a Thymidine Incorporation Assay with the Human Tumor Colony-Forming Assay", *Intl. J. Cell. Cloning*, 1987; 5:421-431.
Weisenthal et al., "Prediction of Drug Resistance in Cancer Chemotherapy: The Kern and DiSC Assays", *Oncology*, 1991; 5(9): 93-103.

(Continued)

*Primary Examiner*—Larry R. Helms
*Assistant Examiner*—Lynn Bristol
(74) *Attorney, Agent, or Firm*—Pillsbury Winthrop Shaw Pittman LLP

(57) ABSTRACT

The present disclosure provides methods for determining the sensitivity of cancerous cells to various anti-cancer therapies and predicting the efficacy of these therapies. Specifically, the present disclosure provides methods for predicting the efficacy of one or more candidate anti-cancer therapies in a patient, based on determining the sensitivity of the patient's cancerous cells after exposure to candidate anti-cancer therapies in vitro. The disclosure further provides methods for predicting the efficacy of candidate anti-cancer therapies by using an in vitro sensitivity test of the patient's cancerous cells and a surrogate in vivo efficacy test of the patient's cancerous cells grafted into a surrogate host. The disclosure further provides methods for selecting the most efficacious anti-cancer therapy(s) for a patient, thereby avoiding ineffective or unnecessary treatments.

2 Claims, 7 Drawing Sheets

OTHER PUBLICATIONS

Falkiewicz et al., "c-myc Oncogene gene dosage, serum CEA and CA-15.3 antigen levels, and cellular DNA values in relation to ex vivo chemosensitivity of primary human breast cancer", *Acta Biochimica Polonica*, 2000; 47(1): 149-156.

Zhou et al., "Drug discovery targeting Chk1 and Chk2 kinases", *Progress in Cell Cycle Research*, 2003; 5: 413-421.

Tenzer et al., "Potentiation of DNA-Damage-Induced Cytotoxicity by $G_2$ Checkpoint Abrogators", *Curr. Med. Chem.—Anti-Cancer Agents*, 2003; 3: 35-46.

\* cited by examiner

| CBDC004 | CBDC401 |
|---|---|
| 4-chloro-benzoic acid 4-methoxy-phenyl ester | 4-chloro-benzoic acid p-tolyl ester |
| CBDC402 | CBDC403 |
| 4-bromo-benzoic acid p-tolyl ester | 3, 4, 5-trifluoro-benzoic acid p-tolyl ester |
| CBDC404 | CBDC405 |
| 4-fluoro-benzoic acid 4-bromo-phenyl ester | 3, 4-dichloro-benzoic acid p-tolyl ester |
| CBDC406 | CBDC407 |
| 2, 4-dichloro-benzoic acid p-tolyl ester | 4-fluoro-benzoic acid p-tolyl ester |

FIGURE 4 (page 1 of 3)

| CBDC408 | | CBDC409 |
|---|---|---|
| 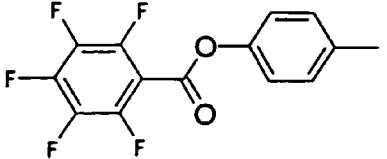 | | 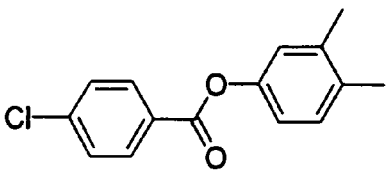 |
| 2, 3, 4, 5, 6-pentafluoro-benzoic acid p-tolyl ester | | 4-chloro-benzoic acid 3, 4-dimethyl-phenyl ester |
| CBDC410 | | CBDC411 |
| 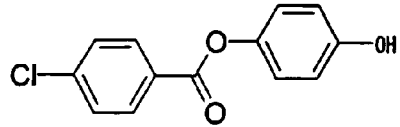 | | 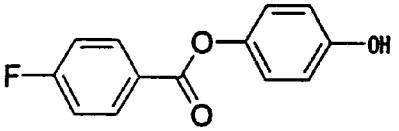 |
| 4-chloro-benzoic acid 4-hydroxy-phenyl ester | | 4-fluoro-benzoic acid 4-hydroxy-phenyl ester |
| CBDC412 | | CBDC413 |
| 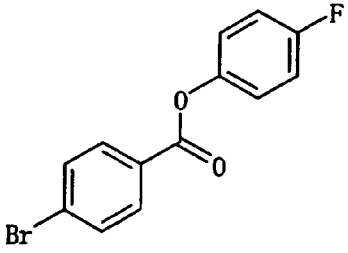 | | 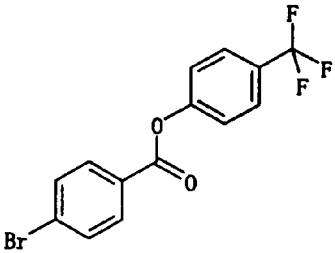 |
| 4- Bromo-benzoic acid 4-fluoro-phenyl ester | | 4-Bromo-benzoic acid 4-trifluoromethyl-phenyl ester |
FIGURE 4, Continued (page 2 of 3)

| | | |
|---|---|---|
| CBDC414 | | CDBC415 |
| 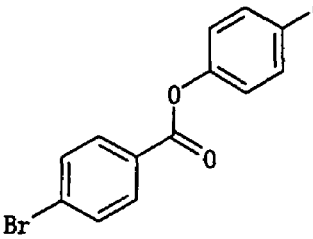 | | 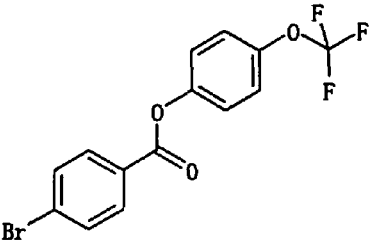 |
| 4-bromo-benzoic acid 4-hydroxy-phenyl ester | | 4-bromo-benzoic acid 4-trifluoromethoxy-phenyl ester |
| CBDC418 | | CDBC440 |
| 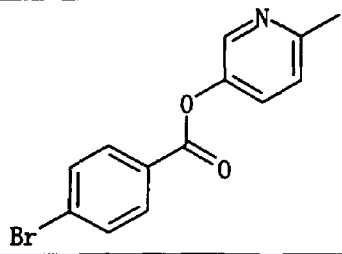 | | 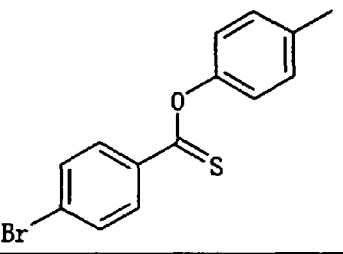 |
| 4-bromo-benzoic acid 6-methyl-pyridin-3-yl ester | | 4-bromo-thiobenzoic acid O-p-tolyl ester |
| CBDC441 | | CDBC442 |
| 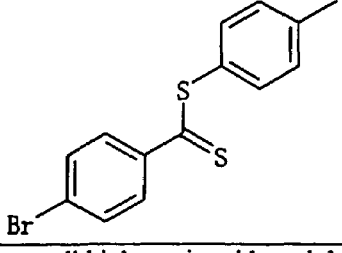 | | 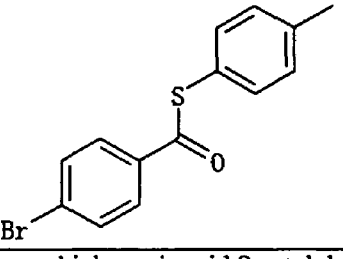 |
| 4-bromo-dithiobenzoic acid p-tolyl ester | | 4-bromo-thiobenzoic acid S-p-tolyl ester |
FIGURE 4, Continued (page 3 of 3)

ern et al., 1987, *Intl J Cell Cloning* 5:421-431), on the

SENSITIVITY TEST TO PREDICT EFFICACY OF ANTI-CANCER THERAPIES

RELATED APPLICATIONS

This application claims benefit of priority to U.S. Provisional Patent Application Ser. No. 60/494,022, filed Aug. 8, 2003.

FIELD OF THE INVENTION

The present disclosure relates to methods for determining the sensitivity of cancerous cells to various therapies. Specifically, the present disclosure relates to methods for predicting the efficacy of one or more candidate anti-cancer therapies in a patient, based on determining the sensitivity of the patient's cancerous cells to various treatment regimens being screened as candidate anti-cancer therapies. The disclosure further relates to methods for selecting the most efficacious anti-cancer therapy(s) for each patient, thereby avoiding unnecessary treatments.

BACKGROUND

Presently, most clinically available anti-cancer therapies produce a desired response in only about 10-50% of human cancerous cells tested, and anti-cancer treatments are often accompanied by unwanted side-effects.

Existing methods for measuring the ability of candidate anti-cancer therapies to inhibit or kill cancerous cells include measuring effects on tetrazolium blue reduction in fresh tumor biopsy materials. (Black et al., 1954, *J Nat Cancer Inst* 14:1147-1158), on cloning of human tumor stem cells, (Salmon et al., 1978, *N Engl J Med* 298:1321-1327), on the uptake of radiolabeled thymidine by tumor cells in the presence and absence of the anti-cancer agent being tested (Kern et al., 1987, *Intl J Cell Cloning* 5:421-431), on the differential staining properties of living and dead cells (Weisenthal et al., 1991, *Oncology*, 5:93-103). The colony formation test is currently favored as a method for determining the effect of a candidate anti-cancer therapy on proliferation of cancerous cells in vitro, although it is understood that tumor cells may not grow well in vitro for a long enough time for the test to be successful. While each of these methods provides some measure of the sensitivity of cancerous cells to a candidate anti-cancer therapy, many of these assays take 1-3 weeks to complete. Generally, neither doctors and patients can wait that long for results.

SUMMARY OF THE INVENTION

This invention provides methods to determine, within a period of 3 to 5 days, the sensitivity of a patient's cancerous cells to various anti-cancer therapies, by measuring the DNA content of cells that have been removed from the patient and exposed to various anti-cancer therapies in vitro. By providing rapid methods for determining the sensitivity of a patient's cancerous cells to various anti-cancer therapies, the present invention provides methods for identifying and selecting the most effective anti-cancer therapies on an individualized basis. By providing rapid methods for determining the sensitivity of a patient's cancerous cells to various anti-cancer therapies, the present invention provides feasible methods for screening as many candidate anti-cancer therapies as desired, in order to identify therapies having desirable qualities such as high selective cytotoxicity towards the patient's cancerous cells and low cytotoxicity towards the patient's non-cancerous cells.

The invention provides methods for determining the sensitivity of a patient's cancerous cells to a candidate anti-cancer therapy by exposing a sample of the patient's cancerous cells to the candidate anti-cancer therapy in vitro, measuring the DNA content of each cancerous cell in the sample after exposure to the candidate anti-cancer therapy, and determining the cell cycle distribution of the sample after exposure to the candidate anti-cancer therapy, where a change in the cell cycle distribution of the sample after exposure to the candidate anti-cancer therapy indicates the patient's cancerous cells are sensitive to the candidate anti-cancer therapy. In particular, the invention provides methods for determining the sensitivity of a patient's cancerous cells to a candidate anti-cancer therapy, wherein an increase in the sub-G1 population in a sample of cancerous cells after exposure to the candidate anti-cancer therapy indicates the therapy is cytotoxic towards the patient's cancerous cells. An increase in the G2/M population in the sample after exposure to the candidate anti-cancer therapy indicates the therapy inhibits proliferation of the patient's cancerous cells.

The invention provides methods for determining the sensitivity of a patient's cancerous cells to a candidate anti-cancer therapy that also include determining the sensitivity of the patient's non-cancerous cells to the candidate anti-cancer therapy.

The invention provides methods for rapidly determining the sensitivity of a patient's cancerous cells to a candidate anti-cancer therapy, by exposing a sample of the patient's cancerous cells to the candidate anti-cancer therapy in vitro, measuring the DNA content of each cancerous cell in the sample after exposure to the candidate anti-cancer therapy, and determining the cell cycle distribution of the sample after exposure to the candidate anti-cancer therapy, where the method is complete within about 3 to about 5 days. The invention provides methods for determining the sensitivity of a patient's cancerous cells to a candidate anti-cancer therapy within about 3 days. The invention provides methods for determining the sensitivity of a patient's cancerous cells to a candidate anti-cancer therapy within about 4 days. The invention provides methods for determining the sensitivity of a patient's cancerous cells to a candidate anti-cancer therapy within about 5 days.

The invention provides methods for determining the sensitivity of a patient's cancerous cells to a plurality of candidate anti-cancer therapies by exposing a plurality of samples of cancerous cells to a plurality of candidate anti-cancer therapies. Methods are provided for ranking the effectiveness of candidate anti-cancer therapies based on the sensitivity of the patient's cancerous cells to each therapy, and for identifying the most effective candidate anti-cancer therapy for the patient.

The invention provides methods for determining the sensitivity of a patient's cancerous cells to a candidate anti-cancer therapy by exposing a sample of the patient's cancerous cells to the candidate anti-cancer therapy in vitro, measuring the DNA content of each cancerous cell in the sample after exposure to the candidate anti-cancer therapy, and determining the cell cycle distribution of the sample after exposure to the candidate anti-cancer therapy, where the anti-cancer therapy can be a DNA-damaging agent or a G2 checkpoint-abrogating agent. The invention provides methods for determining the sensitivity of a patient's cancerous cells to one or more non-peptide G2 checkpoint-abrogating compounds such as 4-Chloro-benzoic acid 4-methoxy-phenyl ester (CDBC004), 4-Chloro-benzoic acid p-tolyl ester (CBDC401); 4-Bromo-benzoic acid p-tolyl ester (CBDC402); 3,4,5-Trifluoro-benzoic acid p-tolyl ester (CBDC403); 4-Fluoro-benzoic acid 4-bromo-phenyl ester; compound with ethane (CBDC404), 3,4-Dichloro-benzoic acid p-tolyl ester; compound with ethane (CBDC405), 2,4-Dichloro-benzoic acid p-tolyl ester; compound with ethane (CBDC406), 4-Fluoro-benzoic acid p-tolyl ester; compound with ethane (CBDC407), 2,3,4,5,6-Pentafluoro-benzoic acid p-tolyl ester; compound with ethane (CBDC408), 4-Chloro-benzoic acid 3,4-dimethyl-phenyl ester; compound with ethane (CBDC409), 4-Chloro-benzoic acid 4-hydroxy-phenyl ester; compound with ethane (CBDC410), 4-Fluoro-benzoic acid 4-hydroxy-phenyl ester; compound with ethane (CBDC411), 4-Bromo-benzoic acid 4-fluoro-phenyl ester (CBDC412), 4-Bromo-benzoic acid 4-trifluoromethyl-phenyl ester (CBDC413), 4-Bromo-benzoic acid 4-hydroxy-phenyl ester (CBDC414), 4-Bromo-benzoic acid 4-trifluoromethoxy-phenyl ester (CBDC415), 4-Bromo-benzoic acid 6-methyl-pyridin-3-yl ester (CBDC418), 4-Bromo-thiobenzoic acid 0-p-tolyl ester (CBDC440), 4-Bromo-dithiobenzoic acid p-tolyl ester (CBDC441), or 4-Bromo-thiobenzoic acid S-p-tolyl ester (CBDC442). The invention provides methods for determining the sensitivity of a patient's cancerous cells to one or more G2 checkpoint-abrogating peptides or peptidomimetics such as CBP500 (SEQ ID NO: 25), CBP501 (SEQ ID NO: 26), CBP504 (SEQ ID NO: 29), CBP505 (SEQ ID NO: 30), CBP506 (SEQ ID NO: 31), CBP510 (SEQ ID NO: 32), CBP511 (SEQ ID NO: 33), CBP512 (SEQ ID NO: 34), or CBP603 (SEQ ID NO: 37).

The invention provides methods for determining the sensitivity of a patient's cancerous cells to a candidate anti-cancer therapy by exposing a sample of the patient's cancerous cells to the candidate anti-cancer therapy in vitro, measuring the DNA content of each cancerous cell in the sample after exposure to the candidate anti-cancer therapy, and determining the cell cycle distribution of the sample after exposure to the candidate anti-cancer therapy, where the anti-cancer therapy is a combination therapy. Combination therapies can include a DNA-damaging agent and a G2 checkpoint-abrogating agent, especially when the combination is selectively cytotoxic towards cancerous cells. Methods are provided for predicting the efficacy of a combination therapy in which the G2 checkpoint-abrogating agent selectively sensitizes cancerous cells to the cytotoxic effects of the DNA-damaging agent. In one combination therapy, the DNA-damaging agent is irinotecan (CPT-11) and the G2 checkpoint-abrogating agent is CBDC402. In another combination therapy, the DNA-damaging agent is irinotecan (CPT-11) and the G2 checkpoint-abrogating agent is CBDC004. In another combination therapy, the DNA-damaging agent is cisplatin (CDDP) and the G2 checkpoint-abrogating agent is CBP501 (SEQ ID NO: 26).

The invention provides methods for determining the sensitivity of a patient's cancerous cells to a candidate anti-cancer therapy that includes measuring the sensitivity of cancerous cells in vitro, and also includes a surrogate in vivo efficacy test of a candidate anti-cancer therapy. The surrogate efficacy test can be a xenograft tumor assay that includes grafting a sample of the patient's cancerous cells into a surrogate host, allowing a tumor to form in the surrogate host, treating the surrogate host with a candidate anti-cancer therapy, and measuring the effects of the candidate anti-cancer therapy on the tumor.

The invention provides methods for predicting the efficacy of an anti-cancer therapy for a patient by exposing a sample of the patient's cancerous cells to the candidate anti-cancer therapy in vitro, determining the cell cycle distribution of the sample of cancerous cells after exposure to the candidate anti-cancer therapy, and determining the cytotoxicity of the candidate anti-cancer therapy towards the patient's cancerous cells. The invention further provides a method for determining the safety of the candidate anti-cancer therapy by exposing a sample of the patient's non-cancerous cells to the candidate anti-cancer therapy in vitro and determining the cytotoxicity of the candidate anti-cancer therapy towards the patient's non-cancerous cells.

The invention provides methods for selecting the most efficacious anti-cancer therapy for a patient by determining the sensitivity of the patient's cancerous and non-cancerous cells to a plurality of candidate anti-cancer therapies, determining the cytotoxicity of each candidate anti-cancer therapy for the patient's cancerous cells and non-cancerous cells, and selecting the therapy having the highest cytotoxicity towards the patient's cancerous cells and the lowest cytotoxicity towards the patient's non-cancerous cells.

BRIEF DESCRIPTION OF THE DRAWINGS

FIG. 4 shows structures and CBDC code names of exemplary G2 checkpoint-abrogating non-peptide compounds used to predict the efficacy of anti-cancer therapies.

Figure 1:
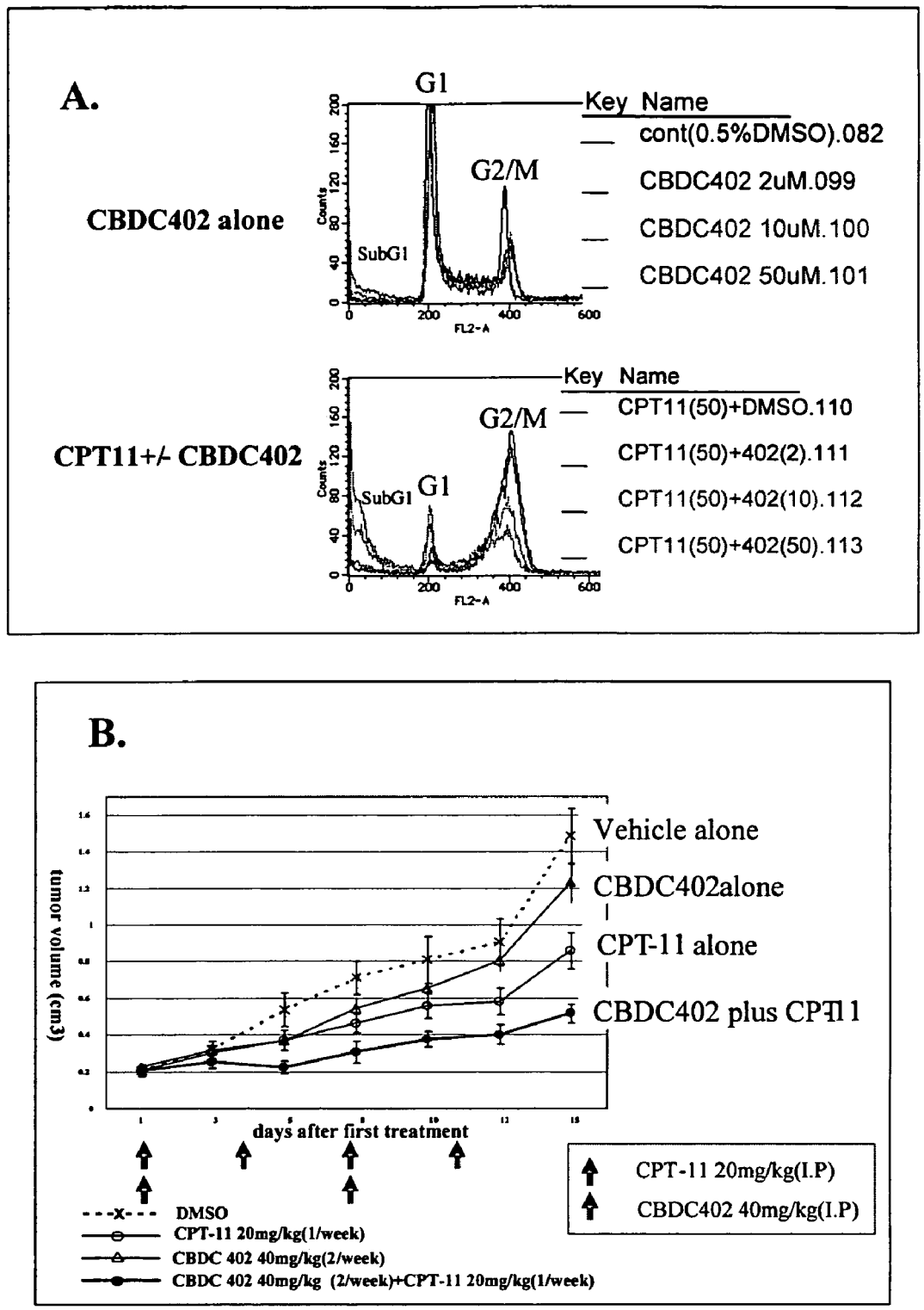
FIG. 1 shows the correlation of an in vitro sensitivity test using flow cytometry (FIG. 1A) and a surrogate in vivo efficacy test using the xenograft tumor assay (FIG. 1B), to test the efficacy of CBDC402, CPT-11, and a combination of CBDC402 and CPT-11 against HCT-116 cells.

Table 1 shows sequences, SEQ ID NOs, and CBP code names of exemplary G2 checkpoint-abrogating peptides and peptidomimetics used to predict the efficacy of anti-cancer therapies.

DETAILED DESCRIPTION OF THE INVENTION

The present disclosure provides methods for determining the sensitivity of cancerous cells to various anti-cancer therapies. In particular, the present disclosure provides methods for predicting the efficacy of various anti-cancer therapies in a patient, based on determining the sensitivity of the patient's cancerous cells to various anti-cancer therapies. The disclosure further provides methods for selecting the most efficacious anti-cancer therapy or therapies for a patient, based on ex vivo methods for determining the sensitivity of the patient's cancerous cells to compounds and/or treatments being screened as candidate anti-cancer therapies. Methods are provided for selecting efficacious anti-cancer therapies with fewer non-specific side effects, as a large number of candidate therapies can be screened to find therapies with a suitable high level of selective cytotoxicity towards the patient's cancerous cells, and an acceptably low level of non-selective cytotoxicity towards the patient's non-cancerous cells. Thus, the present disclosure provides methods for predicting the response of a patient's cancerous cells to various anti-cancer therapies prior to treating the patient, such that the most promising treatment regime for each patient can be selected and unnecessary or ineffective treatments can be avoided. The subject matter of the present application is related to the subject matter of U.S. patent application Ser. No. 10/457,029, filed Jun. 6, 2003, which is hereby incorporated in its entirety.

Unless defined otherwise, all technical and scientific terms used herein have the meaning commonly understood by a person skilled in the art to which this invention belongs. As used herein, the singular forms "a", "and," "the" and "is" include plural referents unless the context clearly indicates otherwise. For example, reference to a "compound" includes a plurality of compounds and reference to "a residue" or an "amino acid" includes reference to one or more residues and amino acids. All publications, patents, and patent applications cited herein are hereby expressly incorporated by reference for all purposes.

Methods to Predict the Efficacy of Anti-Cancer Therapies

The present invention provides methods to predict the efficacy of anti-cancer therapies. In particular, methods are provided to identify those candidate therapies that are effective against proliferative disorders such as cancer, including metastatic and non-metastatic solid or liquid tumors. More particularly, methods are provided to identify those candidate therapies that are most effective for an individual subject, especially a human patient, suffering from a proliferative disorder. Methods as provided herein can likewise be used to treat proliferative disorders such as cancer, including treating metastatic and non-metastatic solid or liquid tumors. As used herein, the terms "proliferative disorder" and "proliferative condition" mean any pathological or non-pathological physiological condition characterized by aberrant or undesirable proliferation of at least one cell, including conditions characterized by undesirable or unwanted cell proliferation or cell survival conditions characterized by deficient or aberrant or deficient apoptosis, as well as conditions characterized by aberrant or undesirable or unwanted cell survival. As used herein, the term "cancer" refers to a proliferative disorder. As used herein, the term "cancerous cell" refers to a cell that is undergoing, or is capable of undergoing, aberrant cell proliferation characteristic of a proliferative disorder such as cancer. As used herein, "anti-cancer therapy" refers to a treatment regime that inhibits, ameliorates, reduces the symptoms of, or eliminates a proliferative disorder, in particular cancer, in a subject. An "anti-cancer therapy" refers to a treatment regime that may include one or more chemical compounds, one or more physical treatments such as radiation, heat, or even surgery, or a combination of chemical compounds and physical treatments. A "candidate anti-cancer therapy" refers to a treatment regime intended to inhibit, ameliorate, reduce the symptoms of, or eliminate a proliferative disorder, in particular cancer, in a subject, where the candidate anti-cancer therapy is being tested in accordance with the methods of the present invention.

Methods as provided herein can be used to identify those candidate anti-cancer therapies that are effective against proliferative disorders such as cancer in any subject that is susceptible to such disorders. The term "subject" refers to animals, typically mammals, such as primates (humans, apes, gibbons, chimpanzees, orangutans, macaques), domestic animals (dogs and cats), farm animals (horses, cattle, goats, sheep, pigs) and experimental animals (mice, rats, rabbits, guinea pigs). Subjects include animal disease models such as tumor-bearing mice or rats, in particular a xenograft mouse model in which human cancer cells are grafted into a mouse and form a tumor. As used herein, the term "patient" refers to a human subject in need of treatment with anti-cancer therapy.

The present invention provides methods that include steps of providing cancerous cells from a subject, contacting cancerous cells with candidate anti-cancer therapies, and determining the DNA content per cell of a sample of cancerous cells exposed to candidate anti-cancer therapies. As disclosed below, determining the DNA content of each cancerous cell in a sample of cells exposed to a candidate anti-cancer therapy makes it possible to determine whether the candidate therapy has the desired cytotoxic or inhibitory effect on cancerous cells. It is understood that methods of the invention generally also include practicing the same steps using non-cancerous (normal) cells from the subject, to determine whether the candidate therapy has a selective effect on cancerous cells. The present invention provides ex vivo methods to determine the sensitivity of a subject's cancerous cells to various anti-cancer therapies, to predict the efficacy and safety of each anti-cancer therapy tested, and to select the most efficacious therapy or therapies in a short time.

Methods as provided herein are suitable for screening candidate anti-cancer therapies to identify the most effective anti-cancer therapy for a particular subject. In accordance with one aspect of the invention, cancerous cells are isolated from a patient, exposed to candidate anti-cancer therapies, and the DNA content of each cell in each sample is determined. This provides an in vitro measurement of the effect of each candidate anti-cancer therapy on the patient's cancerous cells, thereby providing an in vitro prediction of the sensitivity of the patient's cancerous cells to each candidate therapy. In one embodiment, the in vitro method described above is suitable for screening large numbers of candidate anti-cancer therapies to determine their effectiveness against the cancerous cells of a patient. In another embodiment, the in vitro method described above is practiced using cancerous cells from a plurality of patients. In another embodiment, the in vitro method described above is used to screen candidate compounds or treatments for their potential usefulness in anti-cancer therapies. In another embodiment, the in vitro method described above is practiced using cells from a plurality of patients, to screen candidate compounds or treatments for their potential usefulness in anti-cancer therapies.

It is understood that methods of the invention generally also include practicing the same steps using non-cancerous (normal) cells from the subject, to determine whether a candidate therapy has a selective effect on cancerous cells. Measuring the effects on non-cancerous cells can also be used to predict the safety and potential side-effects of a candidate anti-cancer therapy that appears to be effective against a patient's cancerous cells. In one embodiment, the effects on non-cancerous cells are measured for each candidate anti-cancer therapy being tested. In another embodiment, the effects on non-cancerous cells are measured for each candidate anti-cancer therapy that had been identified as having a desired cytotoxic or inhibitory effect on the patient's cancerous cells.

Methods as provided herein are suitable for screening candidate anti-cancer therapies using experimental animal models. In accordance with one aspect, candidate anti-cancer therapies can be screened by measuring the in vitro effects on cancerous cells isolated from animals that are regarded as animal models or surrogates for various proliferative disorders. In particular, candidate anti-cancer therapies can be screened by measuring the in vitro effects on cancerous cells isolated from animals that are regarded as animal models or surrogates for particular types of cancer. In one embodiment, the in vitro screening method is used to screen large numbers of candidate anti-cancer therapies using cells from one or more animal models of a particular type of cancer. In another embodiment, the in vitro screening method is used to screen candidate compounds or treatments for their potential usefulness in anti-cancer therapies, using cells from one or more animal models of a particular type of cancer.

Methods of the present invention are particularly suitable for screening candidate anti-cancer therapies using an in vitro sensitivity test of cells in culture, and a surrogate in vivo efficacy test, which provides at least two ex vivo methods to predict the sensitivity of a patient's cancerous cells to candidate anti-cancer therapies. The xenograft tumor assay provides a suitable surrogate in vivo efficacy test for candidate anti-cancer therapies in accordance with the present invention. Non-limiting examples of embodiments using both an in vitro sensitivity test and a surrogate in vivo efficacy test using the xenograft tumor assay are disclosed in Examples 1, 2, and 3 below. Cancerous cells isolated from a human patient are grown in culture, exposed to one or more candidate anti-cancer therapies, and the DNA content of each cell is measured, providing an in vitro measure of the sensitivity of the patient's cancerous cells to each candidate therapy. In the xenograft tumor assay, cancerous cells isolated from a human patient are grafted into a suitable host (e.g., a mouse) to form a tumor, after which the host animal is treated with candidate anti-cancer therapies and the effects on tumor growth are measured. By measuring the effects of candidate anti-cancer therapies on the grafted human tumor in the host, the xenograft tumor assay provides a second, surrogate in vivo measure of the sensitivity of the patient's cancerous cells to each candidate therapy, without having to expose the human patient to the candidate therapy. It is understood that non-cancerous cells can also be isolated from the patient and tested using the in vitro method described above, to determine the safety and potential side-effects of candidate anti-cancer therapies.

Methods including both an in vitro sensitivity test and a surrogate in vivo assay provide a safe and effective way to predict the sensitivity of a patient's cancerous cells to candidate anti-cancer therapies, especially in a clinical setting. In addition, such methods provide confirmation of in vitro results and provide a surrogate assay system for detecting possible side effects. Finally, such methods provide means for calibrating screening assays by measuring the in vitro and surrogate in vivo effects of a standard treatment and comparing these with the in vitro and surrogate in vivo effects of a candidate anti-cancer therapy, especially a novel or previously untested candidate anti-cancer therapy.

The present invention provides methods for designing anti-cancer therapies that are tailored to the patient and should provide a more favorable response rate. In addition, the present invention provides methods to avoid the use of unnecessary, unsafe, or less effective anti-cancer therapies in the patient, thereby avoiding or minimizing unwanted side-effects.

In accordance with one aspect, the methods of the present invention provide cost efficiencies by providing guidance for selecting and using only those anti-cancer therapies to which the patient's cancerous cells are sensitive, thereby avoiding therapies that are not likely to be successful for the patient. By avoiding treatments that are not likely to be successful, the patient is protected from suffering side-effects of ineffective treatments. In various embodiments, the sensitivity of a patient's cancerous cells can be determined in about 2, 3, 4, 5, 6, 7, 8, 9, or 10 days after the cells have been removed from the patient. In certain embodiments, the sensitivity of a patient's cancerous cells can be determined in about 3 to 5 days after removal from the patient.

Cells for Testing

In accordance with one aspect, cancerous cells are provided by isolating cells from a subject, in particular a human patient, using methods that include but are not limited to, taking peripheral blood, aspirating bone marrow, tissue (tumor) biopsy, or removing cancerous cells surgically, e.g., during an operation to remove a tumor or other cancerous tissue. If non-cancerous cells are also being tested in a particular embodiment, these cells can be isolated from a subject from a suitable location. If necessary, cells can be further manipulated before being exposed to one or more candidate anti-cancer therapies, e.g., cell clumps may be enzymatically digested to prepare a single cell suspension, or cell populations may be expanded in vitro using cell culture. The methods of the present invention can be employed to test cancerous cells from a wide variety of cancers (carcinomas, neoplasms, proliferative disorders), including but not limited to, ovarian cancer, bladder cancer, lung cancer including small-cell lung cancers, cervical cancer, breast cancer, prostate cancer, gliomas, fibrosarcomas, retinoblastomas, melanomas, soft tissue sarcomas, osteosarcomas, leukemias, stomach cancer, colon cancer, carcinoma of the kidney, gastrointestinal cancer, salivary gland cancer, pancreatic cancer, Hodgkin's disease, non-Hodgkin's lymphomas, acute and chronic lymphocytic leukemias, multiple myeloma, neuroblastoma, Wilms' tumor, testicular cancer, soft-tissue sarcomas, chronic lymphocytic leukemia, primary macroglobulinemia, chronic granulocytic leukemia, primary brain carcinoma, malignant pancreatic insulinoma, malignant carcinoid carcinomas, malignant melanomas, choriocarcinomas, mycosis fungoides, head and neck carcinomas, osteogenic sarcoma, pancreatic carcinomas, acute granulocytic leukemia, hairy cell leukemia, neuroblastoma, rhabdomyosarcoma, Kaposi's sarcoma, genitourinary carcinomas, thyroid carcinomas, esophageal carcinomas, malignant hypercalcemia, cervical hyperplasia, renal cell carcinomas, endometrial carcinomas, polycythemia vera, essential thrombocytosis, adrenal cortex carcinomas, skin cancer, and prostatic carcinomas. It is understood that one of skill in the art can adapt the teaching provided herein to test the efficacy of candidate anti-cancer therapies against other cancers not listed here. It is likewise understood that one of skill in the art can practice the methods provided herein to test the efficacy of candidate anti-cancer therapies using suitable animal models of any proliferative disorder.

In accordance with one aspect, methods are provided for separately analyzing the DNA content of a sample of normal (non-cancerous) cells and a sample of cancerous cells, to increase the accuracy of the in vitro sensitivity test. In one embodiment, cancerous cells and normal (non-cancerous) cells are removed from discrete locations and the samples are kept separate at all times. In a sample having both normal and cancerous cells present, the cells can be distinguished by a variety of methods including using antibodies or other probes that distinguish between normal and cancerous cells, detecting aneuploidy in cancerous cells, or observing morphological differences between normal and cancerous cells.

In one embodiment, normal and cancerous cells in a mixed sample are sorted into separate samples prior to analysis of DNA content to determine cell cycle stage. In another embodiment, normal and cancerous cells in a mixed sample are analyzed, and the cell type (normal or cancerous) is distinguished at the same time the DNA content of each cell is measured.

Methods are provided herein to separately analyze the effects of anti-cancer therapies on cancerous cells isolated from different cancers. In accordance with one aspect, the effects of candidate anti-cancer therapies are evaluated separately for cancerous cell samples isolated from different locations. In one embodiment, cancerous cell samples are taken from cancerous tissues at different locations within a patient's body in order to determine whether cancerous cells from different locations have equivalent sensitivity. In one embodiment, cancerous cells are isolated from discrete tumors found at different locations in the body. In one embodiment, cancerous cells are isolated from cancers that exist in more than one form, e.g., a cancer that has formed solid tumors in some locations and is also circulating in blood or lymph. In another embodiment, cancerous cells are isolated from different locations within a cancerous tissue, e.g., from multiple locations within a single tumor, or from liver, lung, or breast tissue with growths of cancerous cells at multiple locations within the tissue. In accordance with another aspect, samples of cancerous cells are taken from a plurality of patients diagnosed with the same type of cancer, in order to compare the sensitivity of cancerous cells of the same type isolated from different individuals.

Determining the Cell Cycle in a Sample

The present invention provides methods for determining the sensitivity of a subject's cancerous cells to candidate anti-cancer therapies by measuring the effects on cell cycle distribution as described below. A shift in the cell cycle distribution of a sample after exposure to a candidate anti-cancer therapy indicates that the cells in the sample were sensitive to the therapy. By measuring the DNA content of each cell in a sample and determining the cell cycle stage of each cell, it is possible to determine the number of cells in the sample that are in each of the normal cell cycle stages (G0/G1, S, and G2/M), as well as the number of dead ("sub-G1") and aneuploid cells in the sample. Thus, "determining the cell cycle distribution in a sample" refers to determining the proportion of cells in the sample that are in normal cell cycle stages (G0/G1, S, and G2/M), as well as the proportion of dead ("sub-G0") cells and aneuploid cells in the sample In accordance with the present invention, the DNA content and cell cycle stage of each cell in a sample of cells treated with candidate anti-cancer therapies can be determined using compositions and methods that include staining cell DNA with compounds that bind to DNA stoichiometrically and emit a detectable signal proportional to the amount DNA in the nucleus, and then determining the DNA content per cell using any method suitable for the DNA-staining compound selected. Suitable compounds include but are not limited to, propidium iodide (PI), bromodeoxyuridine (BrdU), Hoechst dye (especially Hoechst 33342), Cyber Green, mithramycin, DAPI, or other DNA-staining compounds known in the art. The DNA content of cells can be analyzed using variety of approaches such as flow cytometry, laser scanning cytometry and other suitable methods known in the art and described in the Examples below and, in, e.g., Givan, *Flow Cytometry: First Principles* (Wiley, 2002) or Shapiro, *Practical Flow Cytometry, 4th Edition* (Wiley, 2003).

The DNA content of a cell can be used as an indicator of the cell cycle stage of the cell, where DNA content is proportional to fluorescence intensity of fluorochromes that bind stoichiometrically to DNA, such as propidium iodide (PI). In a sample, the distribution of cells in each of the G1, (first gap), S (DNA synthesis), G2/M (second gap/mitosis) phases of the cell cycle can be determined by measuring the nuclear DNA content of each cell in the population. The DNA content of G2/M cells is twice that of G1 cells. S-phase cells are distributed between the G1 and G2/M populations. Non-cycling cells are considered to be in the G0 phase.

Mathematical processes, including but not limited to deconvolution, are employed to transform the measurements of DNA content into representations of the cell cycle distribution of cells in the sample. One common method of representing cell cycle distribution is to generate "histograms" showing the number of cells having a particular DNA content. Generally, representations of clusters of histograms representing populations of cells having similar DNA content will form what look like "peaks" clustered around a certain value. DNA histograms of normal (non-cancerous) cells are usually dominated by a large, normally-distributed (Gaussian) peak representing the DNA content of diploid G0/G1 cells. Because the DNA content of cancerous cells often varies from the normal DNA content, samples of cancerous cells often show in a second G0/G1 peak at a different horizontal (x-axis) location on the DNA histogram. The appearance of two G0/G1 peaks (or more) is an important feature in establishing that DNA-content abnormalities are present. Populations of non-cycling, or cell-cycle-arrested populations are often devoid of S-phase and G2/M cells, while cycling populations have a large proportion of S-phase and G2/M cells. Cell-cycle-arrested cancerous cells may sometimes be identified as that population of cells in which the number of cells present in S-phase and G2/M is significantly reduced, and/or, in which the number of cells present in G0/G1 is significantly increased, with respect to other cell populations.

Dead cells and aneuploid cells can also be identified on the basis of their DNA content. During apoptosis (cell death), DNA becomes fragmented by endonucleases and these small DNA fragments can leak out from the cells, resulting in a reduced total DNA content that is lower than in the G1 phase. Thus, the "sub-G1" fluorescence peak is understood to indicate the number of dead cells in a population.

In accordance with the present invention, changes in the cell cycle distribution in a sample after exposure to a candidate anti-cancer therapy indicates that the cells are sensitive to the therapy. Particular changes in cell cycle distribution can be used as indicators of the mode of action of anti-cancer therapy on sensitive cells. An increased sub-G1 population in a sample that has been exposed to a candidate anti-cancer therapy is understood to indicate the therapy was cytotoxic towards the cells in the sample. In particular, an increased sub-G1 population in a sample of cancerous cells exposed to a candidate anti-cancer therapy is understood to indicate the therapy was cytotoxic to the cancerous cells. An increase in the G2/M population in a sample after exposure to the candidate anti-cancer therapy is understood to indicate the therapy inhibits proliferation (division, mitosis) of the cells in the sample. In particular, an increase in the G2/M population in a sample of cancerous cells after exposure to the candidate anti-cancer therapy is understood to indicate the therapy inhibits proliferation of the cancerous cells.

In certain embodiments, an anti-cancer therapy that is cytotoxic towards a patient's cancerous cells is preferred. In other embodiments, an anti-cancer therapy that inhibits proliferation of a patient's cancerous cells is preferred. In other embodiments, anti-cancer therapies having other effects on sensitive cancerous cells would be preferred. One of skill in the art can determine the preferred mode(s) of action of an anti-cancer therapy sought for a particular embodiment.

As noted above, normal (non-cancerous) cells are generally also exposed to candidate anti-cancer therapies and their DNA content is also measured, as a "control" to determine the selectivity of the anti-cancer therapy. In accordance with this aspect of the invention, an increased sub-G1 population in a sample of normal (non-cancerous) cells after exposure to a candidate anti-cancer therapy indicates non-selective cytotoxicity. Conversely, an increased sub-G1 population in a sample of cancerous cells, and little or no increase in the sub-G1 population in a sample of normal (non-cancerous) cells from the same patient indicates selective cytotoxicity of the candidate anti-cancer therapy towards cancerous cells from the patient being studied. It is understood that anti-cancer therapies with selective cytotoxicity towards cancerous cells are preferred.

Measurement of Additional Parameters

In accordance with another aspect of the present invention, methods for determining the efficacy of candidate anti-cancer agents optionally include measuring other parameters besides DNA content. In some cases, additional measurements can be used to more precisely determine the target of a candidate anti-cancer therapy. If desired, cancerous cells can be labeled with, e.g., antibodies specific for the type of cancer being studied. Likewise, one of skill in the art can measure other characteristic features of the cancer being studied, e.g., gene expression or enzymatic activity that characterizes the cancerous cells being studied. Gene expression can be measured using methods known in the art, including but not limited to, determining the levels of specific mRNA or protein. Protein levels may be analyzed by, e.g., Western blotting with specific antisera, or by measuring the activity of the encoded protein, e.g. by employing DNA gel shift assays to detect activity of cancer-related transcription factors, or by analyzing the expression of genes known to be activated by such factors. Expression can also be measured by measuring gene transcription, e.g., by Northern blotting with specific probes to detect mRNA transcriptions. Measuring characteristic features of the cancerous cells being studied can provide confirmation of the identity of these cells. In addition, measuring characteristic features may also indicate what characteristic feature is targeted by a candidate anti-cancer therapy.

It is also possible to make additional measurements of other effects of a candidate anti-cancer therapy. By way of example, cell size and morphology can be used to provide additional cues to identify cancerous cells in cell cycle arrest. Small cancerous cells in a sample may be cell-cycle-arrested cancerous cells, and their size allows them to be differentiated from (larger) malignant counterparts. With respect to cancerous cell morphology, cell-cycle-arrested cancerous cells may also be identified as those cells which generally have nuclei with an inactive appearance, such as nuclei with clumped chromatin, or nuclei with absent or conspicuous nucleoli. Cancerous cells can be identified as being under cycle arrest based upon the expression of certain key genes such as cellular proto-oncogene. For example, decreased expression of the c-myc gene may be one indication of an arrested cell. The increased expression of genes encoding AP1 transcription factors, such as c-jun, and even more particularly, c-fos, is also considered to be characteristic of cell-cycle-arrested cancerous cells. In certain embodiments, measurements of cell-cycle-arrested cancerous cells may be useful for identifying candidate anti-cancer therapies that arrest but do not kill a particular type of cancerous cell from a particular patient.

Anti-Cancer Therapies

The present invention provides methods for predicting the efficacy of anti-cancer treatments for a subject by determining the sensitivity of the subject's cancerous cells to the anti-cancer therapy. In accordance with the methods of the present invention, cancerous cells are contacted with candidate anti-cancer therapies using methods including but not limited to, culturing cancerous cells in vitro in the presence or absence of candidate anti-cancer chemical compounds, or treating in vitro cultured cancerous cells with candidate anti-cancer physical treatments. Anti-cancer therapies suitable for use in the methods of the invention include, but are not limited to, DNA-damaging agents, G2 checkpoint-abrogating non-peptide compounds, G2 checkpoint-abrogating peptides and peptidomimetics, and combination therapies. One of skill in the art can use the methods of the present invention to evaluate the effectiveness of candidate anti-cancer therapies not recited here, and develop an individualized treatment plan for a patient based on the results obtained by practicing the methods of the present invention.

Anti-Cancer Therapies: DNA-Damaging Agents

Anti-cancer therapies suitable for use in the methods of the present invention include DNA-damaging agents, which include any treatment regimen that directly or indirectly damages DNA. DNA-damaging agents including chemical compounds and physical treatments that are known to cause DNA damage and/or are identified by a screening method, e.g., as described in U.S. patent application Ser. No. 09/667, 365. Specific examples of DNA-damaging agents include, but are not limited to, 5-fluorouracil (5-FU), rebeccamycin, bleomycin, cisplatin, hyperthermia, UV irradiation, gamma-irradiation, alpha irradiation, high temperature, alkylating agents, nitrosoureas, anti-metabolites, plant alkaloids, plant extracts, radioisotopes, capecitabine, S-1 (Tegafur, 5-chloro-2,4-dihydroxypyridine and oxonic acid), 5-ethynyluracil, arabinosyl cytosine (ara-C), 5-azacytidine (5-AC), 2',2'-difluoro-2'-deoxycytidine (dFdC), purine antimetabolites (mercaptopurine, azathiopurine, thioguanine), gemcitabine hydrochlorine (Gemzar), pentostatin, allopurinol, 2-fluoro-arabinosyl-adenine (2F-ara-A), hydroxyurea, sulfur mustard (bischloroetyhylsulfide), mechlorethamine, melphalan, chlorambucil, cyclophosphamide, ifosfamide, thiotepa, AZQ, mitomycin C, dianhydrogalactitol, dibromoducitol, alkyl sulfonate (busulfan), nitrosoureas (BCNU, CCNU, 4-methyl CCNU or ACNU), procarbazine, decarbazine, anthracyclins such as doxorubicin (adriamycin; ADR), daunorubibcin (Cerubicine), idarubicin (Idamycin) and epirubicin (Ellence), anthracyclin analogues such as mitoxantrone, actinimycin D, non intercalating topoisomerase inhibitors such as epipodophyllotoxins (etoposide=VP16, teniposide=VM-26), podophyllotoxin, bleomycin (Bleo), pepleomycin, compounds that form adducts with nucleic acid including platinum derivatives, e.g., cisplatin (CDDP), trans analogue of cisplatin, carboplatin, iproplatin, tetraplatin and oxaliplatin, as well as camptothecin, topotecan, irinotecan (CPT-11), and SN-38. Specific examples of nucleic acid damaging treatments include radiation e.g., ultraviolet (UV), infrared (IR), or α-, β-, or γ-radiation, as well as environmental shock, e.g., hyperthermia. One of skill in the art can identify and use other DNA-damaging agents and treatments suitable for use in the methods of the present invention.

Anti-Cancer Therapies: G2 Checkpoint-Abrogating Agents

In accordance with another aspect of the invention, methods are provided for testing and predicting the efficacy of G2 checkpoint-abrogating agents, including but not limited to non-peptide G2 checkpoint-abrogating non-peptide compounds disclosed in U.S. patent application Ser. No. 10/457,029, and G2 checkpoint-abrogating peptides and peptidomimetics disclosed in U.S. patent application Ser. No. 10/347,145 and in the U.S. patent application entitled "Peptides and peptidomimetics having immune-modulating, anti-inflammatory, and anti-viral activity" filed Jun. 25, 2004, entire disclosure of each of which is hereby incorporated by reference.

The term "abrogate the G2 checkpoint" or "G2 checkpoint-abrogating," or any grammatical equivalent of the term, refers to the ability to abrogate the ability of a cell to arrest the cell cycle at the G2 checkpoint. The G2 cell cycle checkpoint restricts the onset of mitosis until DNA replication and repair are complete, and disruption of the G2 checkpoint would allow premature onset of mitosis prior to the completion of DNA replication and repair. Without wishing to be limited to this theory, it is believed that, in cells that have accumulated DNA damage, abrogation of the G2 checkpoint means the cells do not have an opportunity to correct or repair DNA damage at the G2 checkpoint and instead, proceed through G2 without DNA repair, which leads to mitotic catastrophe, apoptosis, or other conditions resulting in cell suppression or cell death. As used herein, the term "apoptosis" refers to programmed cell death, and associated changes in cell physiology, including nucleic acid fragmentation, caspase activation, chromosome condensation, etc., as is understood in the art. The term "mitotic catastrophe" means cell death resulting from an error in the mitotic process.

Abrogation of the cell cycle G2 checkpoint includes abrogation under conditions in the cell that otherwise would cause G2 cell cycle arrest, such as the accumulation of DNA damage by, e.g., certain anti-tumor agents, X-ray irradiation, gamma-ray irradiation, UV irradiation, or hyperthermia. Abrogation of the G2 checkpoint under such conditions is considered "abrogation of the G2 checkpoint" but more particularly, abrogation of "the DNA-damage-induced G2 checkpoint," where it is understood that the DNA-damage-induced G2 checkpoint includes recognition of DNA damage and generation of a signal that normally produces G2 cell cycle-arrest. A cell in which the cell cycle G2 checkpoint is abrogated exhibits a decrease in the length of time that the cell is in the G2 checkpoint, which can range from absence of G2 checkpoint altogether (G2 checkpoint arrest) to a G2 checkpoint having a decrease in duration of minutes, hours, days, weeks or longer under appropriate conditions. Thus, a cell contacted with a compound of the invention has a G2 checkpoint time shorter in length than the cell normally would have in the absence of the compound. For example, a decrease in the length of G2 checkpoint time would mean that a cell which is in G2 for a certain time, e.g., 4 hours, when contacted with an invention compound, is in G2 for less than 4 hours, e.g., 3.5, 3, 2.5, 2, 1 or fewer hours. The term "G2 abrogation" or "G2 checkpoint abrogation" or "G2 checkpoint inhibitory activity" or any grammatical equivalent, means any amount of abrogation or inhibition of the G2 checkpoint.

The present invention provides methods for testing the sensitivity of cancerous cells to G2 checkpoint-abrogating agents. In accordance with the aspect of the invention, G2 checkpoint-abrogating agents are screened or evaluated as candidate anti-cancer therapies. Cancerous cells can be contacted with G2 checkpoint-abrogating agents using methods including, but not limited to, culturing cancerous cells in vitro in the presence or absence of the G2 checkpoint-abrogating agents, or treating in vitro cultured cancerous cells with the G2 checkpoint-abrogating agents.

G2 Abrogating Non-Peptide Compounds

The invention provides methods for predicting the sensitivity of a subject's cancerous cells, in particular a human patient's cancerous cells, to G2 checkpoint-abrogating non-peptide compounds that, when administered to a cell, abrogate the G2 checkpoint, in particular the DNA-damage-induced G2 checkpoint, and kill or suppress cells. It is understood that G2 checkpoint-abrogating non-peptide compounds, e.g., as disclosed in U.S. patent application Ser. No. 10/457,029, can kill or suppress cells with or without DNA-damaging treatment.

The present invention provides methods for screening and evaluating G2 checkpoint-abrogating non-peptide compounds as candidate anti-cancer therapies, wherein the compounds have the following general structure:

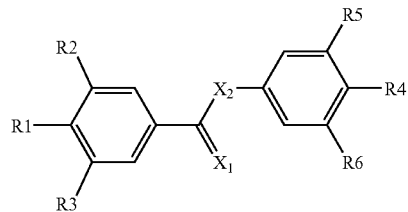

where either or both benzenes can be substituted with pyrazine, pyrimidine. piperazine, morpholine, cyclohexane, piperizine or pyridine; R1 is a halogen such as bromine (Br), chlorine (Cl), fluorine (F), Iodine (I), amino (NH$_2$), nitro (NO$_2$), hydroxy (OH) O-methyl (OCH$_3$) methyl (CH$_3$) or hydrogen (H), R2, R3, R4, R5 and/or R6 is bromine (Br), chlorine (Cl), fluorine (F), Iodine (I), amino (NH$_2$), nitro (NO$_2$), methyl (CH$_3$), O-Methyl (OCH$_3$), hydroxy (OH), CH(CH$_3$)$_2$, CHO, CHOCH$_3$, O(CH$_2$)nCH$_3$, OCO(C$_6$H$_{12}$)Cl, COOCH$_3$ or hydrogen; X1 is nitrogen (NH), oxygen (O) or sulfate (S); X2 is oxygen (O) or sulfate (S). Illustrative embodiments are found in FIG. 4, but compounds of the invention are not limited to these embodiments.

The invention further provides methods for screening and evaluating G2 checkpoint-abrogating non-peptide compounds as candidate anti-cancer therapies, wherein the compounds have the following general structure:

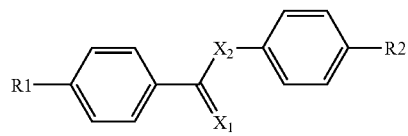

where either or both benzenes can be substituted with pyrazine, pyrimidine. piperazine, morpholine, cyclohexane, piperizine or pyridine; R1 is bromine (Br), chlorine (Cl), fluorine (F), Iodine (I), amino (NH$_2$), nitro (NO$_2$), hydroxy (OH) O-methyl (OCH₃) methyl (CH₃) or hydrogen (H), R2 is bromine (Br), chlorine (Cl), fluorine (F), Iodine (I), amino (NH₂), nitro (NO₂), methyl (CH₃), O-Methyl (OCH₃), hydroxy (OH), CH(CH₃)₂, CHO, CHOCH₃, O(CH₂)nCH₃, OCO(C₆H₁₂)Cl, COOCH₃ or hydrogen; X1 is nitrogen (NH), oxygen (O) or sulfate (S); X2 is oxygen (O) or sulfate (S). Illustrative embodiments are found in FIG. 4.

The invention further provides methods for screening and evaluating G2 checkpoint-abrogating non-peptide compounds as candidate anti-cancer therapies, wherein the compounds have the following general structure:

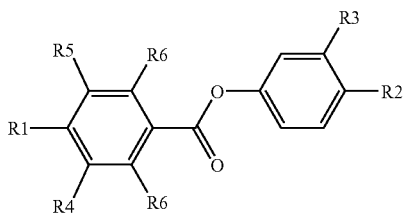

wherein substitution of different molecules at positions R1 to R6 affects the G2-checkpoint-abrogating activity of the resulting compounds. The following structure-activity relations have been determined At R1, bromine (Br) provides higher activity than chlorine (Cl), fluorine (F) or methyl (CH₃).

At R2, methyl (CH₃) or O-Methyl (OCH₃) provide higher activity than hydroxide (OH), bromine (Br), chloride (Cl), CH(CH₃)₂, CHO, CHOCH₃, O(CH₂)nCH₃, OCO(C₆H₁₂)Cl or COOCH₃ or H.

At R3, methyl (CH₃) provided higher activity than H or O-Methyl (OCH₃).

At R4, bromine (Br), fluorine (F), chlorine (Cl), or H can be used.

At R5, bromine (Br), fluorine (F), chlorine (Cl), or H can be used.

At R6, bromine (Br), fluorine (F), chlorine (Cl), or H can be used.

The foregoing list is merely illustrative and not exhaustive. Illustrative embodiments are found in FIG. 4. One of skill in the art can make additional substitutions and activity determinations according to the teachings of the present disclosure, to obtain additional compounds of the invention. It is understood by one of skill in the art that, although certain substitutions have been observed to produce structures with higher activity than other structures with respect to DNA-damage-induced G2 checkpoint abrogation, the invention provides compounds with all substitutions and all levels of activity. For a particular embodiment, one of skill will consider multiple factors in selecting a compound of the invention for use in that embodiment, in addition to the activity of a compound against a particular target. One of skill in the art will consider activity of the compound, availability, stability, ease or efficiency of synthesis, suitability for formulation in a pharmaceutical composition, drugability, interaction with other compounds in vivo, ex vivo, or in vitro, ability to kill cells, ability to suppress growth of cells, effects on normal cells, and other activities.

The invention provides methods for predicting the efficacy of a G2 checkpoint-abrogating non-peptide compound as an anti-cancer therapy, by determining the sensitivity of a subject's cancerous cells, in particular a patient's cancerous cells, to the G2 checkpoint-abrogating non-peptide compound. The invention provides methods for determining the sensitivity of a subject's cancerous cells to compounds that selectively abrogate the DNA-damage-induced cell cycle G2 checkpoint in G1 checkpoint-defective cells such as cancer cells, and selectively abrogate the DNA-damage-induced G2 checkpoint in cells treated with DNA-damaging agents. The invention further provides methods for determining the sensitivity of a subject's cancerous cells to compounds that inhibit xenograft tumor growth, alone or in combination with other anti-cancer therapies. The invention provides methods for determining the sensitivity of a subject's cancerous cells to compounds that suppress colony formation in vitro in cancerous cells, alone or in combination with other anti-cancer therapies. In particular, the invention provides methods for determining the sensitivity of a subject's cancerous cells to compounds that abrogate the G2 checkpoint and/or suppress or kill cancer cells, including but not limited to:

CDBC004: 4-Chloro-benzoic acid 4-methoxy-phenyl ester
CBDC401: 4-Chloro-benzoic acid p-tolyl ester
CBDC402: 4-Bromo-benzoic acid p-tolyl ester
CBDC403: 3,4,5-Trifluoro-benzoic acid p-toly 1 ester
CBDC404: 4-Fluoro-benzoic acid 4-bromo-phenyl ester; compound with ethane
CBDC405: 3,4-Dichloro-benzoic acid p-tolyl ester; compound with ethane
CBDC406: 2,4-Dichloro-benzoic acid p-tolyl ester; compound with ethane
CBDC407: 4-Fluoro-benzoic acid p-tolyl ester; compound with ethane
CBDC408: 2,3,4,5,6-Pentafluoro-benzoic acid p-tolyl ester; compound with ethane
CBDC409: 4-Chloro-benzoic acid 3,4-dimethyl-phenyl ester; compound with ethane
CBDC410: 4-Chloro-benzoic acid 4-hydroxy-phenyl ester; compound with ethane
CBDC411: 4-Fluoro-benzoic acid 4-hydroxy-phenyl ester; compound with ethane
CBDC412: 4-Bromo-benzoic acid 4-fluoro-phenyl ester
CBDC413: 4-Bromo-benzoic acid 4-trifluoromethyl-phenyl ester
CBDC414: 4-Bromo-benzoic acid 4-hydroxy-phenyl ester
CBDC415: 4-Bromo-benzoic acid 4-trifluoromethoxy-phenyl ester
CBDC418: 4-Bromo-benzoic acid 6-methyl-pyridin-3-yl ester
CBDC440: 4-Bromo-thiobenzoic acid O-p-tolyl ester
CBDC441: 4-Bromo-dithiobenzoic acid p-tolyl ester
CBDC442: 4-Bromo-thiobenzoic acid S-p-tolyl ester Structures of these compounds are provided in FIG. 4.

G2 Checkpoint-Abrogating Peptides and Peptidomimetics

The invention provides methods for predicting the sensitivity of a subject's cancerous cells, in particular a human patient's cancerous cells, to G2 checkpoint-abrogating peptides and peptidomimetics as disclosed U.S. patent application Ser. No. 10/347,145 and in the U.S. patent application entitled "Peptides and peptidomimetics having immune-modulating, anti-inflammatory, and anti-viral activity" filed Jun. 25, 2004, as candidate anti-cancer therapies.

The present invention provides methods for screening and evaluating G2 checkpoint-abrogating peptides and peptidomimetics as candidate anti-cancer therapies, in particular CBP peptides and peptidomimetics having a structure that includes regions A (residues P1 to P5) and B (residues P6 to P11) arranged to form any of the following structures: P1,P2,P3,P4,P5,P6,P7,P8,P9,P 10,P11 (SEQ ID NO: 1) or P6,P7,P8,P9,P 10,P11,P1,P2,P3,P4,P5 (SEQ ID NO: 2), or P1,P2,P3,P4,P5 (SEQ ID NO: 3) where P1 and P5 are benzoyl-phenylalanine (Bpa), or tyrosine (Tyr), or phenylalanine (Phe), or cyclohexyl alanine (Cha), or phenylalanine with fluorine at positions 2,3,4,5, and 6 on the phenyl residue (Phe-2,3,4,5,6-F), or TyrTyr, or PhePhe, or ChaPhe-2,3,4,5, 6-F or a moiety that occupies a similar side chain space as that occupied by one or two benzene-like or cyclohexane-like side chain structures, where the moiety can be one or two amino acids or amino acid structural/functional analogues, including non-natural amino acids, synthetic amino acids, amino acid mimetics, and chimeric molecules. Positions P2 and P4 are any amino acid, and P3 is tryptophan (Trp) or any moeity that occupies a similar side chain space as that occupied by the Trp side chain. Positions P6, P7, P8, P9, P10, P11 include arginine (Arg) at five or more positions when P2 and/or P3 are not Arg, and any non-Arg position can be any amino acid or nothing. When P2 and/or P3 are Arg, then P6-P11 can contain fewer than five Arg.

The invention further provides methods for screening and evaluating G2 checkpoint-abrogating CBP peptides and peptidomimetics as candidate anti-cancer therapies, wherein the CBP compounds include: CBP500 (SEQ ID NO: 25); CBP501 (SEQ ID NO: 26); CBP504 (SEQ ID NO: 29); CBP505 (SEQ ID NO: 30); CBP506 (SEQ ID NO: 31); CBP510 (SEQ ID NO: 32); CBP511 (SEQ ID NO: 33); CBP512 (SEQ ID NO: 34); CBP603 (SEQ ID NO: 37). The sequence of each of the preceding CBP compounds is disclosed in Table 1, below.

The invention further provides methods for screening and evaluating G2 checkpoint-abrogating CBP peptides and peptidomimetics as candidate anti-cancer therapies, wherein the CBP compounds include have the general structure: P1,P2,P3,P4,P5 P6,P7,P8,P9,P10,P11 (SEQ ID NO: 1) or P6,P7,P8,P9,P10,P11,P1,P2,P3,P4,P5 (SEQ ID NO: 2) structure described above, and have G2 checkpoint abrogating activity similar to that of compound CBP501 (SEQ ID NO: 26). One of skill in the art can adapt the teachings provided herein to screen and evaluate other G2 checkpoint-abrogating peptides and peptidomimetics as candidate anti-cancer therapies.

TABLE 1

Sequences, SEQ ID NOs, and CBP code names of exemplary peptides and peptidomimetics

| Sequence of Peptides and Peptidomimetics | SEQ ID NO | CBP Code Name |
|---|---|---|
| (1-Tyr)(1-Gly)(1-Arg)(1-Lys)(1-Lys)(1-Arg)(1-Arg)(1-Gln)(1-Arg)(1-Arg)(1-Arg)(1-Cha)(1-Phe-2,3,4,5,6-F)(1-Arg)(1-Ser)(1-Pro)(1-Ser)(1-Tyr)(1-Tyr) | SEQ ID NO: 4 | CBP413 |
| (1-Tyr)(1-Gly)(1-Arg)(1-Lys)(1-Lys)(1-Arg)(1-Arg)(1-Gln)(1-Arg)(1-Arg)(1-Arg)(1-Cha)(1-Phe-2,3,4,5,6-F)(1-Arg)(1-Ser)(1-Pro)(1-Ser)(1-Tyr) | SEQ ID NO: 5 | CBP420 |
| (1-Arg)(1-Arg)(1-Arg)(1-Cha)(1-Phe-2,3,4,5,6-F)(1-Arg)(1-Ser)(1-Pro)(1-Ser)(1-Tyr)(1-Tyr) | SEQ ID NO: 6 | CBP430 |

TABLE 1-continued

Sequences, SEQ ID NOs, and CBP code names of exemplary peptides and peptidomimetics

| Sequence of Peptides and Peptidomimetics | SEQ ID NO | CBP Code Name |
|---|---|---|
| (1-Arg)(1-Arg)(1-Gln)(1-Arg)(1-Arg)(1-Arg)(1-Cha)(1-Phe-2,3,4,5,6-F)(1-Arg)(1-Ser)(1-Pro)(1-Ser)(1-Tyr)(1-Tyr) | SEQ ID NO: 7 | CBP431 |
| (1-Arg)(1-Arg)(1-Gln)(1-Arg)(1-Arg)(1-Arg)(1-Cha)(1-Phe-2,3,4,5,6-F)(d-Ser)(d-Trp)(1-Pro)(1-Ser)(1-Tyr) | SEQ ID NO: 8 | CBP432 |
| (1-Tyr)(1-Gly)(1-Arg)(1-Lys)(1-Lys)(1-Arg)(1-Arg)(1-Gln)(1-Arg)(1-Arg)(1-Arg)(1-Cha)(1-Phe-2,3,4,5,6-F)(1-aminoundecanoic acid)(1-Tyr)(1-Tyr) | SEQ ID NO: 9 | CBP440 |
| (d-Tyr)(d-Tyr)(d-Ser)(1-Gly)(d-Ser)(d-Arg)(d-Phe-2,3,4,5,6-F)(d-Cha)(d-Arg)(d-Arg)(d-Arg)(d-Gln)(d-Arg)(d-Arg)(d-Lys)(d-Lys)(d-Arg)(1-Gly)(d-Tyr) | SEQ ID NO: 10 | CBP450 |
| (d-Tyr)(d-Ser)(d-Pro)(1-Trp)(Ser)(d-Phe-2,3,4,5,6-F)(d-Cha)(d-Arg)(d-Arg)(d-Arg)(d-Gln)(d-Arg)(d-Arg) | SEQ ID NO: 11 | CBP451 |
| (d-Tyr)(d-Ser)(1-Pro)(1-Trp)(Ser)(d-Phe-2,3,4,5,6-F)(d-Cha)(d-Arg)(d-Arg)(d-Arg)(d-Gln)(d-Arg)(d-Arg) | SEQ ID NO: 12 | CBP452 |
| (d-Tyr)(d-Ser)(d-Pro)(1-Trp)(Ser)(d-Phe-2,3,4,5,6-F)(d-Pro)(d-Arg)(d-Arg)(d-Arg)(d-Gln)(d-Arg)(d-Arg) | SEQ ID NO: 13 | CBP454 |
| (d-Tyr)(d-Ser)(1-Pro)(1-Trp)(Ser)(d-Phe-2,3,4,5,6-F)(1-Pro)(d-Arg)(d-Arg)(d-Arg)(d-Gln)(d-Arg)(d-Arg) | SEQ ID NO: 14 | CBP455 |
| (1-Tyr)(1-Tyr)(1-aminoundecanoic acid)(d-Phe-2,3,4,5,6-F)(d-Cha)(d-Arg)(d-Arg)(d-Arg)(d-Gln)(d-Arg)(d-Arg)(d-Lys)(d-Lys)(d-Arg)(1-Gly)(d-Tyr) | SEQ ID NO: 15 | CBP460 |
| (1-Tyr)(1-aminoundecanoic acid)(d-Phe-2,3,4,5,6-F)(d-Cha)(d-Arg)(d-Arg)(d-Arg)(d-Gln)(d-Arg)(d-Arg)(d-Lys)(d-Lys)(d-Arg)(1-Gly)(d-Tyr) | SEQ ID NO: 16 | CBP461 |
| (1-Tyr)(1-aminoundecanoic acid)(d-Phe-2,3,4,5,6-F)(d-Cha) | SEQ ID NO: 17 | CBP462 |
| (1-aminoundecanoic acid)(d-Phe-2,3,4,5,6-F)(d-Cha)(d-Arg)(d-Arg)(d-Gln)(d-Arg)(d-Arg)(d-Lys)(d-Lys)(d-Arg)(1-Gly)(d-Tyr) | SEQ ID NO: 18 | C8P463 |
| (1-aminoundecanoic acid)(d-Phe-2,3,4,5,6-F)(d-Cha) | SEQ ID NO: 19 | CBP464 |
| (1-aminoundecanoic acid)(d-Phe-2,3,4,5,6-F)(d-Cha)(d-Arg)(d-Arg)(d-Arg)(d-Gln)(d-Arg)(d-Arg) | SEQ ID NO: 20 | C8P465 |

TABLE 1-continued

Sequences, SEQ ID NOs, and CBP code names of exemplary peptides and peptidomimetics

| Sequence of Peptides and Peptidomimetics | SEQ ID NO | CBP Code Name |
|---|---|---|
| (1-8-aminocaprylic acid)(d-Cha)(d-Phe-2,3,4,5,6-F)(d-Arg)(d-Arg)(d-Arg)(d-Gln)(d-Arg)(d-Arg) | SEQ ID NO: 21 | CBP466 |
| (d-Phe-2,3,4,5,6-F)(d-Cha) | SEQ ID NO: 22 | CBP470 |
| (d-Cha)(d-Phe-2,3,4,5,6-F)(d-Arg)(d-Arg)(d-Arg)(d-Gln)(d-Arg)(d-Arg) | SEQ ID NO: 23 | CBP471 |
| (d-Tyr)(d-Ser)(d-Ser)(d-Trp)(d-Ser)(d-Phe-2,3,4,5,6-F)(d-Cha)(d-Arg)(d-Arg)(d-Arg)(d-Gln)(d-Arg)(d-Arg) | SEQ ID NO: 24 | CBP481 |
| (d-Tyr)(d-Bpa)(d-Ser)(d-Trp)(d-Ser)(d-Phe-2,3,4,5,6-F)(d-Cha)(d-Arg)(d-Arg)(d-Arg)(d-Gln)(d-Arg)(d-Arg) | SEQ ID NO: 25 | CBP500 |
| (d-Bpa)(d-Ser)(d-Trp)(d-Ser)(d-Phe-2,3,4,5,6-F)(d-Cha)(d-Arg)(d-Arg)(d-Arg)(d-Gln)(d-Arg)(d-Arg) | SEQ ID NO: 26 | CBP501 |
| (d-Bpa)(1-8-aminocaprylic acid)(d-Cha)(d-Phe-2,3,4,5,6-F)(d-Arg)(d-Arg)(d-Arg)(d-Gln)(d-Arg)(d-Arg) | SEQ ID NO: 27 | CBP502 |
| (d-Bpa)(1-8-aminocaprylic acid)(d-Phe-2,3,4,5,6-F)(d-Cha)(d-Arg)(d-Arg)(d-Arg)(d-Gln)(d-Arg)(d-Arg) | SEQ ID NO: 28 | CBP503 |
| (d-Asp)(d-Bpa)(d-Ser)(d-Trp)(d-Ser)(d-Phe-2,3,4,5,6-F)(d-Cha)(d-Arg)(d-Arg)(d-Arg)(d-Gln)(d-Arg)(d-Arg) | SEQ ID NO: 29 | CBP504 |
| (d-Bpa)(d-Asp)(d-Ser)(d-Trp)(d-Ser)(d-Phe-2,3,4,5,6-F)(d-Cha)(d-Arg)(d-Arg)(d-Arg)(d-Gln)(d-Arg)(d-Arg) | SEQ ID NO: 30 | CBP505 |
| (d-Bpa)(d-Ser)(d-Trp)(d-Ser)(d-Asp)(d-Phe-2,3,4,5,6-F)(d-Cha)(d-Arg)(d-Arg)(d-Arg)(d-Gln)(d-Arg)(d-Arg) | SEQ ID NO: 31 | CBP506 |
| (d-Arg)(d-Arg)(d-Arg)(d-Gln)(d-Arg)(d-Arg)(d-Cha)(d-Phe-2,3,4,5,6-F)(d-Ser)(d-Trp)(d-Ser)(d-Bpa) | SEQ ID NO: 32 | CBP510 |
| (d-Arg)(d-Arg)(d-Arg)(d-Gln)(d-Arg)(d-Arg)(d-Bpa)(d-Ser)(d-Trp)(d-Ser)(d-Phe-2,3,4,5,6-F)(d-Cha) | SEQ ID NO: 33 | CBP511 |
| (d-Arg)(d-Arg)(d-Arg)(d-Arg)(d-Arg)(d-Arg)(d-Cha)(d-Phe-2,3,4,5,6-F)(d-Ser)(d-Trp)(d-Ser)(d-Bpa) | SEQ ID NO: 34 | CBP512 |
| (d-Bpa)(d-Ser)(d-Trp)(d-Ser)(d-Bpa)(d-Cha)(d-Arg)(d-Arg)(d-Arg)(d-Gln)(d-Arg)(d-Arg) | SEQ ID NO: 35 | CBP601 |
| (d-Bpa)(1-8-aminocaprylic acid)(d-Bpa)(d-Cha)(d-Arg)(d-Arg)(d-Arg)(d-Gln)(d-Arg)(d-Arg) | SEQ ID NO: 36 | CBP602 |
| (d-Bpa)(d-Ser)(d-Trp)(d-Ser)(d-Phe4No2)(d-Cha)(d-Arg)(d-Arg)(d-Arg)(d-Gln)(d-Arg)(d-Arg) | SEQ ID NO: 37 | CBP603 |
| (d-Bpa)(d-Pro)(d-Trp)(d-Pro)(d-Phe4NO2)(d-Cha)(d-Arg)(d-Arg)(d-Arg)(d-Gln)(d-Arg)(d-Arg) | SEQ ID NO: 38 | CBP604 |
| (d-Bpa)(d-Pro)(d-Trp)(d-Pro)(d-Phe4NO2)(d-Nal2)(d-Arg)(d-Arg)(d-Arg)(d-Gln)(d-Arg)(d-Arg) | SEQ ID NO: 39 | CBP605 |
| (d-Phe4NO2)(d-Pro)(d-Trp)(d-Pro)(d-Phe4NO2)(d-Cha)(d-Arg)(d-Arg)(d-Arg)(d-Gln)(d-Arg)(d-Arg) | SEQ ID NO: 40 | CBP606 |
| (d-Bpa)(d-Ser)(d-Trp)(d-Ser)(d-Phe-2,3,4,5,6-F)(d-Cha)(d-Arg)(d-Arg)(d-Arg)(d-Arg)(d-Arg) | SEQ ID NO: 41 | CBP607 |
| (d-Bpa)(d-Ser)(d-Trp)(d-Ser)(d-Phe-2,3,4,5,6-F)(d-Cha)(d-Arg)(d-Arg)(d-Arg)(d-Arg)(d-Arg)(d-Arg) | SEQ ID NO: 42 | CBP608 |
| (d-Bpa)(d-Ser)(d-Trp)(d-Ser)(d-Phe-2,3,4,5,6-F)(d-Cha)(d-Lys)(d-Lys)(d-Lys)(d-Lys)(d-Lys)(d-Lys) | SEQ ID NO: 43 | CBP609 |
| (d-Arg)(d-Arg)(d-Bpa)(d-Arg)(d-Arg)(d-Arg)(d-Phe-2,3,4,5,6-F)(d-Cha) | SEQ ID NO: 44 | CBP700 |
| (d-Arg)(d-Arg)(d-Arg)(d-Bpa)(d-Arg)(d-Trp)(d-Arg)(d-Phe-2,3,4,5,6-F)(d-Cha) | SEQ ID NO: 45 | CBP701 |
| (d-Arg)(d-Arg)(d-Arg)(d-Arg)(d-Bpa)(d-Arg)(d-Trp)(d-Arg)(d-Phe-2,3,4,5,6-F)(d-Cha) | SEQ ID NO: 46 | CBP702 |
| (d-Arg)(d-Arg)(d-Arg)(d-Bpa)(d-Arg)(d-Arg)(d-Arg)(d-Phe-2,3,4,5,6-F)(d-Cha) | SEQ ID NO: 47 | CBP703 |
| (d-Bpa)(d-Cys)(d-Trp)(d-Arg)(d-Phe-2,3,4,5,6F)(d-Cha)(d-Cys) | SEQ ID NO: 48 | CBP524 |
| (d-Tyr)(d-Cys)(d-Pro)(d-Trp)(d-Arg)(d-Phe-2,3,4,5,6F)(d-Cha)(d-Cys) | SEQ ID NO: 49 | CBP721 |

Anti-Cancer Therapies: Combination Therapies

In accordance with another aspect of the invention, methods are provided for predicting the efficacy of anti-cancer treatments for a subject by determining the sensitivity of the subject's cancerous cells to combination therapies. In accordance with one aspect, the present invention provides methods for testing a combination therapy that includes a DNA-damaging agent and a G2 checkpoint-abrogating agent. In one embodiment, a combination therapy includes DNA-damaging agent CPT-11 (camptothecan-11, a topoisomerase inhibitor also known as irinotecan or camptostar) and CBDC402. In another embodiment, a combination therapy includes CPT-11 and CBDC004. In another embodiment, a combination therapy includes DNA-damaging agent CDDP (an alkylating agent also known as cisplatin) and G2 checkpoint-abrogating peptide CBP501 (SEQ ID NO: 26).

In accordance with one aspect of the invention, methods are provided for testing the efficacy of combination therapies in which the cytotoxicity of DNA-damaging agents towards cancerous cells is potentiated or enhanced by G2 checkpoint-abrogating agents, including G2 checkpoint-abrogated non-peptide compounds and G2 checkpoint-abrogating peptides and peptidomimetics, as disclosed herein. Without wishing to be limited by this theory, it is understood that G2 checkpoint-abrogating agents can selectively sensitize cancerous cells to the cytotoxic effects of DNA-damaging agents with little or no cytotoxic effect on normal cells. Many conventional anti-cancer agents target proliferating cells irrespective of whether they are cancerous cells or normal cells, with the result that many conventional anti-cancer therapies give rise to side-effects such as nausea, diarrhea, or hair loss. In contrast, G2 checkpoint-abrogating agents selectively target cells with DNA damage (e.g., impaired cell cycle checkpoints), and therefore have little or no cytotoxic effect on normal cells. Accordingly, the present invention provides methods for screening and evaluating combination therapies for the ability of G2 checkpoint-abrogating agents to potentiate the effects DNA-damaging treatments.

In accordance with another aspect of the invention, methods are provided for identifying the most effective combination therapies. As disclosed in the exemplary illustration in Example 3, a combination therapy of CBP501 (SEQ ID NO: 26) and cisplatin (CDDP) had a higher level of anti-cancer activity than either treatment alone. As shown in Example 3, in vitro results using human cancerous cells in culture showed that each compound alone (CBP501 and cisplatin) had some anti-cancer efficacy, but the combination of compounds had a more pronounced anti-cancer effect. Using the xenograft tumor assay, human cancerous cells were grafted into a host mouse, where they generated tumors that provided a surrogate "in vivo" test of the efficacy of candidate anti-cancer therapies. Tumors were then treated "in vivo" by administering candidate anti-cancer therapies to the mouse host and measuring the effects on tumor size. The in vivo results using the xenograft tumor assay confirmed the prediction of the in vitro results that a combination of CBP501 and CDDP was more effective than either compound alone.

A number of embodiments of the invention have been described. Nevertheless, it will be understood that various modifications may be made without departing form the spirit and scope of the invention. Accordingly, the following examples are intended to illustrate but not limit the scope of the invention described in the claims.

EXAMPLES

Example 1

Correlation of In Vitro Sensitivity Test and In Vivo Efficacy Test Using CBDC402

Cells from a human colon cancer derived cell line HCT-116 were used in an in vitro sensitivity test that measures DNA content of cells by flow cytometry, and in an in vivo efficacy test that measures xenograft tumor growth. The effects of conventional anti-cancer therapy CPT-11, novel candidate anti-cancer therapy CBDC402, a combination of the two compounds, or control treatments (vehicle), were measured in each test system and compared.

In vitro sensitivity test: HCT-116 cells (from ATCC) were cultured in McCOY5A medium (Sigma Chemical Co.) with L-glutamine (Sigma Chemical Co.), penicillin-streptomycin, and 10% fetal calf serum at 37° C. in 5% $CO_2$/air. Cultured cells (at $1.6 \times 10^5$) were pelleted by centrifugation, and then re-suspended and incubated in 300 μl Krishan's solution (0.1% sodium citrate, 50 μg/ml propidium iodide, 20 μg/ml RNase A, 0.5% Nonidet P-40) for 1 h at 4° C. The quantity of DNA in each cell was determined using a fluorescence activated cell scanner (FACScan® Beckton Dickinson, Mountain View, Calif.), and results were analyzed using CELLQuest® software (Beckton Dickinson).

The DNA content of each cell was measured at 24 hr. CBDC402 treatment alone (2, 10, or 50 μM for 3 hr) did not alter the DNA content of HCT-116 cells in vitro (FIG. 1A; upper panel). CPT-11 treatment (50 μM for 3 h) changed the cell cycle distribution dramatically, where the population of cells in G1 phase decreased and the population of cells in G2/M phase increased. This result indicated that cells were arrested at G2/M phase of the cell cycle (proliferation was inhibited) but the cells were not killed, because there was no increase in the sub-G1 population. HCT-116 cells exposed to a combination treatment of both CPT-11 (50 μM for 3 hr) and CBDC402 (2, 10, 50 μM for 3 hr) showed a decrease in the accumulation of both the CPT-11-induced G2/M population and G1 population, and also showed an increase in the subG1 (dead cell) population (FIG. 1A, lower panel), indicating that the combination treatment was cytotoxic to HCT-116 cells.

These results of the in vitro sensitivity test gave rise to the prediction that CBDC402 alone would not suppress HCT-116 xenograft tumor growth in vivo, that CPT-11 would suppress tumor growth moderately, and that a combination of CBDC402 and CPT-11 will suppress tumor growth most efficiently.

Surrogate in vivo efficacy test: FIG. 1B shows the results of the surrogate in vivo efficacy test involving a xenograft tumor assay. HCT-116 cells were implanted by subcutaneous injection of the cells into male SCID mice (Severe Combined Immunodeficient mice, Charles River Lab., Wilmington, Mass.). Treatment was initiated when the tumor size reached about 0.2 $cm^3$ in size. The size of tumors was measured three times per week, using calipers. Tumor volumes were calculated as follows: volume ($cm^3$)=[width $(mm)^2 \times$length (mm)]/2000. Mean tumor sizes (volumes) with standard deviation were plotted (FIG. 1b). Animals were housed in accordance with guidelines from American Association for Laboratory Animal Care and the protocols were approved by institutional animal care committee of CanBas Co. Ltd Established HCT-116 xenografts (0.2 $cm^3$) in SCID mice were treated for two weeks by intraperitoneal injection of the following: vehicle alone (DMSO, two times per week), CBDC402 (40 mg/kg; two times per week), CPT-11 (20 mg/kg; one time per week) or the combination of CBDC402 (two times per week) and CPT-11 (one time per week). As shown in FIG. 1(b), CPBC402 alone did not suppress tumor growth significantly, CPT-11 had moderate tumor suppressive activity, and CBDC402 plus CPT-11 showed strong tumor suppressive activity. The results correlate with the prediction based on results from the in vitro sensitivity test using CBDC004 as described above.

Example 2

Correlation of In Vitro Sensitivity Test and In Vivo Efficacy Test Using CBDC004

Cells from a human colon cancer derived cell line HCT-116 were used in an in vitro sensitivity test that measures DNA content of cells by flow cytometry, and in an in vivo efficacy test that measures xenograft tumor growth. The effects of conventional anti-cancer therapy CPT-11, novel candidate anti-cancer therapy CBDC004, a combination of the two compounds, or control treatments (vehicle), were measured in each test system and compared.

Figure 2:
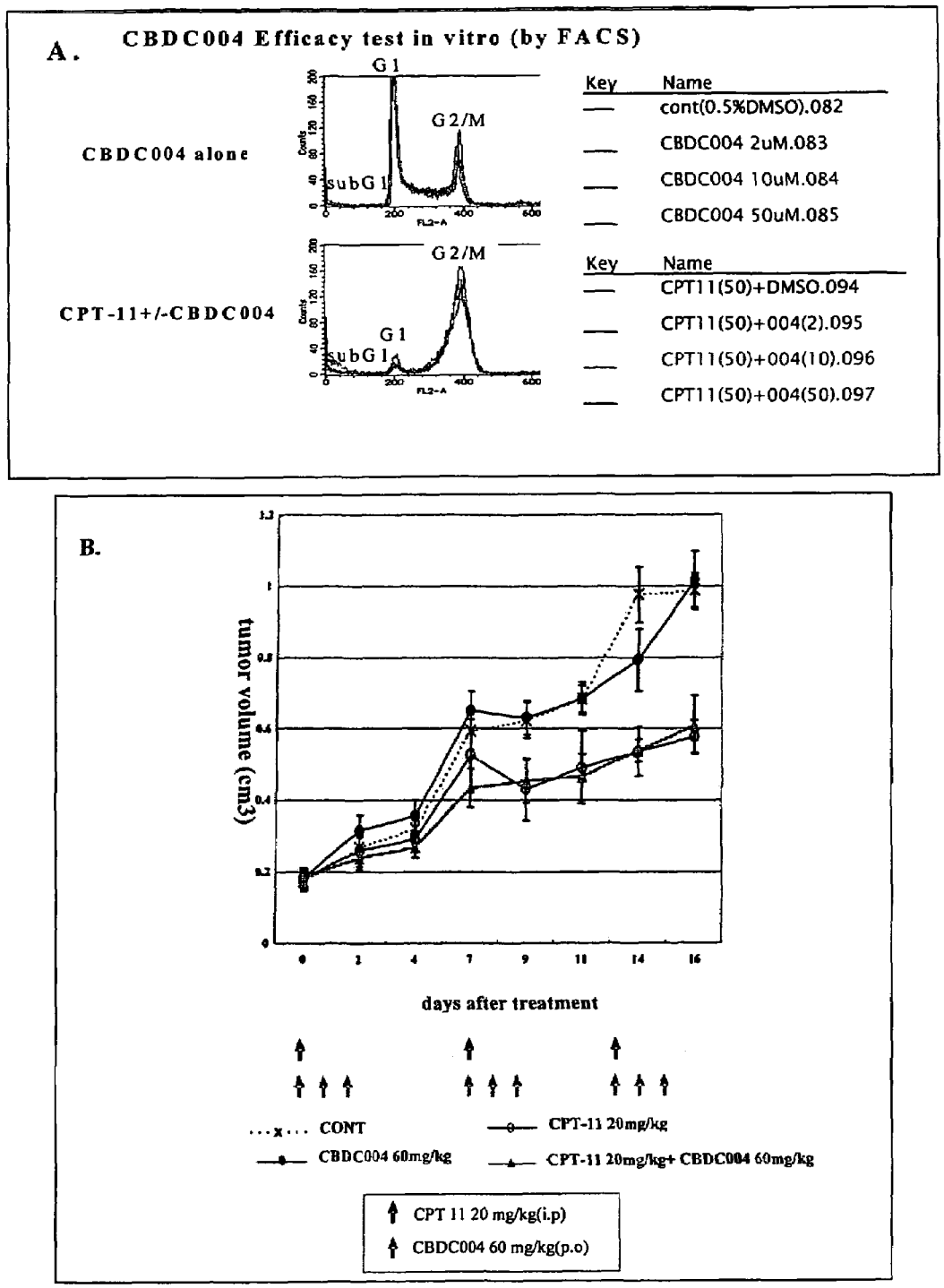
FIG. 2 shows the correlation of an in vitro sensitivity test using flow cytometry (FIG. 2A) and a surrogate in vivo efficacy test using the xenograft tumor assay (FIG. 2B) to test the efficacy of CBDC004, CPT-11, and a combination of CBDC004 and CPT-11 against HCT-116 cells.

In vitro sensitivity test: The in vitro sensitivity test using HCT-116 cells and flow cytometry was carried out as described above, with the modification that CBDC004 was used instead of CBDC402. The DNA content of each cell was measured at 24 hr. CBDC004 treatment alone (2, 10, 50 µM for 3 hr) did not alter the DNA content HCT-116 cells in vitro (FIG. 2A, upper panel). CPT-11 treatment alone (3 hr; 501 µM) changed the cell cycle distribution dramatically, where the population of cells in G I phase decreased and the population of cells in G2/M increased. This indicated that the cells were arrested at G2/M phase of the cell cycle but not killed, because there was no increase in the sub-G1 population. HCT-116 cells exposed to a combination treatment of both CPT-11 (50 µM for 3 hr) and CBDC004 (2, 10, or 50 µM for 3 hr) did not change the DNA content more than CPT-11 alone (FIG. 2A, lower panel).

The results of the in vitro sensitivity test gave rise to the prediction that CBDC004 alone would not suppress HCT-116 xenograft tumor growth in vivo, that CPT-11 would suppress it moderately, and a combination of CBDC004 and CPT-11 would suppress it at same extent to CPT-11 alone.

Surrogate in vivo efficacy test: A surrogate in vivo efficacy test measuring the effects of various compounds on HCT-116 xenograft tumor growth was carried out as described above, with the modification that CBDC004 was used instead of CBDC402.

Established HCT-116 xenografts (0.2 cm$^3$) in SCID mice were treated for two weeks by intraperitoneal injection of the following: vehicle alone (DMSO, two times per week), CBDC004 (30 mg/kg; three times per week), CPT-11 (20 mg/kg; one time per week) or the combination of CBDC402 (two times per week) and CPT-11 (one time per week). As shown in FIG. 2B, CBDC004 did not suppress tumor growth, alone or in combination with PCT-11, and CPT-11 had moderate tumor suppressive activity. The results correlate with the prediction based on results from the in vitro sensitivity test using CBDC004 as described above.

Example 3

Simulation of Sensitivity Test for Clinical Applications

As a simulation of the sensitivity test for the clinical situation, established xenograft tumors of MIAPaCa2 cells in SCID mice were extracted from the mice and cultured in vitro in the presence or absence of a conventional anti-cancer therapy and a novel candidate anti-cancer therapy CBP501 (SEQ ID NO: 26), according to the protocol as follows.

Protocol:

Day 1 Preparation of a Single Cell Suspension from Extracted Xenograft Tumor.

Xenograft tumors of MIAPaCa2 cells were excised from xenograft tumor bearing mice and place in a 10 cm plate with 10 ml of complete culture medium (DMEM (Dainihonseiyaku Co., Osaka, Japan) with 2.5% horse serum (Invitrogen Co., Carlsbad, Calif.) for MIAPaCa2 with 10% fetal calf serum (Equitech-bio, Kerrville, Tex.) at 37° C. with 5% $CO_2$/air). The tissue was sliced into small pieces and non-tumor tissue was removed to the extent possible. The sliced pieces were placed in another 10 cm plate with complete culture medium and minced with a razor blade. The cells were then dispersed in culture medium by pipetting, and centrifuged for 5 min at 1200×g.

The cell pellet was then incubated in buffer containing collagenase for 2 hours at 37° C. After centrifuging a second time, the cell pellet was incubated in buffer containing trypsin for 5 min at room temperature, then suspended in the culture medium, passed through nylon mesh, and re-centrifuged. Pelleted cells were resuspended and the resuspended cells were seeded onto chamber slides and cultured overnight in an incubator.

Day 2 Treating Cells with Anti-Cancer Therapy.

Cells in chamber slides were treated with anti-cancer therapies or control treatments as follows: control solution, CBP501 (SEQ ID NO: 26) at 10 µM, cisplatin (CDDP) at 10 µg/ml, or a combination of CBP501 and cisplatin were added to chamber slides and incubated for 3 hours. Culture medium was changed and chamber slides were cultured for an additional 24 to 48 hours.

Day 3, 4 or 5 Staining and Analysis.

At the beginning of the designated day (day 3, 4, or 5), medium was aspirated from chamber slides and cells were fixed by addition of 70% ethanol followed by incubation for 15 minutes at room temperature. The supernatant was discarded, and phosphate buffered saline with 50 µg/ml propidium iodide (Sigma, St. Louis, Mo.) with 0.1% RNase (Sigma) was added to the slides and incubated for 30 minutes at room temperature. Cells on the chamber slides were then analyzed by Laser Scanning Cytomery (LSC® System, with Olympus microscope).

Results

Figure 3A:
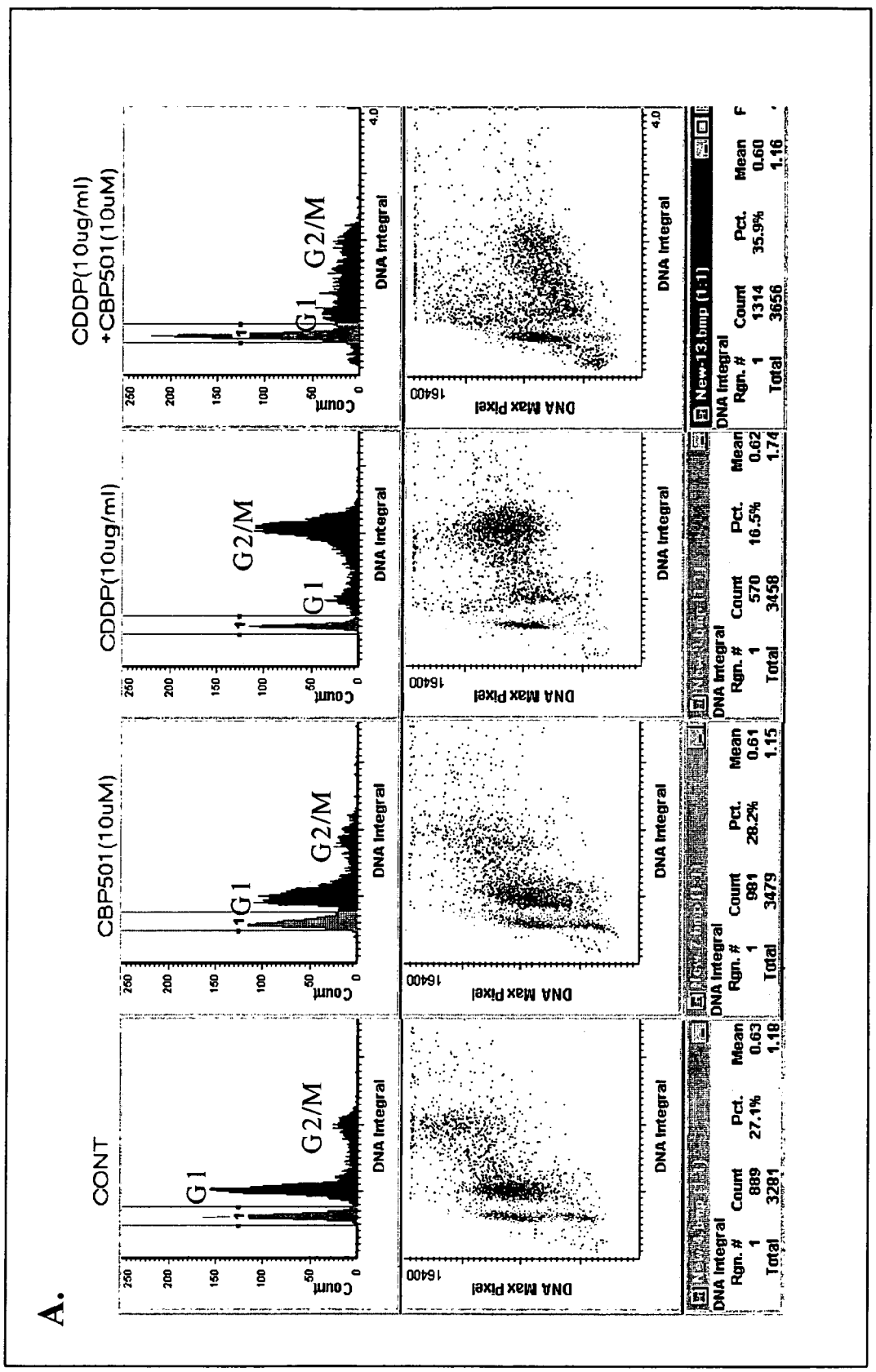
FIG. 3 shows a simulation of the sensitivity test for clinical applications, comparing results from an in vitro sensitivity test using laser scanning cytometry of cultured xenograft tumor cells on chamber slides (FIG. 3A) and a surrogate in vivo efficacy test using the xenograft tumor assay, to test the efficacy of CBP501 (SEQ ID NO: 26), cisplatin (cisdiaminedichloroplatinum, CDDP) or a combination of CBP501 and cisplatin against MIAPaCa2 cells (FIG. 3B).

As shown in FIG. 3A, treatment with CBP501 (SEQ ID NO: 26) broadens the shape of histogram of DNA content values (especially the histogram corresponding to cells in G1 phase), but the cell cycle distribution was not significantly altered. Treatment with cisplatin (CDDP) resulted in accumulation of cells in G2/M phase. Treatment with a combination of CBP501 and cisplatin dramatically decreased both the G1 and G2/M peaks and increased the sub-G1 population, indicating cell death. The peak marked "1" (between the vertical lines) in each histogram indicates the G1 population of non-cancerous mice normal fibroblast cells contaminating the cell culture. Direct observation of cell morphology showed that the combination treatment resulted in a dramatic increase in cell death in the population of tumor cells.

These results gave rise to the prediction that either CBP501 (SEQ ID NO: 26) or cisplatin (CDDP) treatment would have some effect on tumor cells, but a combination treatment with both CBP501 and cisplatin would be more effective than either treatment alone, and a combination treatment would be very effective against tumor cells.

Surrogate in vivo efficacy test: A surrogate in vivo efficacy test using the xenograft tumor assay was carried out as described above, with modifications. MIAPaCa2 cells (n=5) were implanted by subcutaneous injection of the cells to male SCID mice (Charles River Lab., Wilmington, Mass.). Treatment was initiated when tumor size reached about 0.15 cm$^3$ in size. The size of tumors was measured three times per week, using calipers. Tumor volumes were calculated as follows: volume (cm$^3$)=[width (mm)$^2$×length (mm)]/2000.

Mean tumor sizes (volumes) with standard deviation were plotted (FIG. 1b). Animals were housed in accordance with guidelines from American Association for Laboratory Animal Care and the protocols were approved by institutional animal care committee of CanBas Co. Ltd.

Figure 3B:
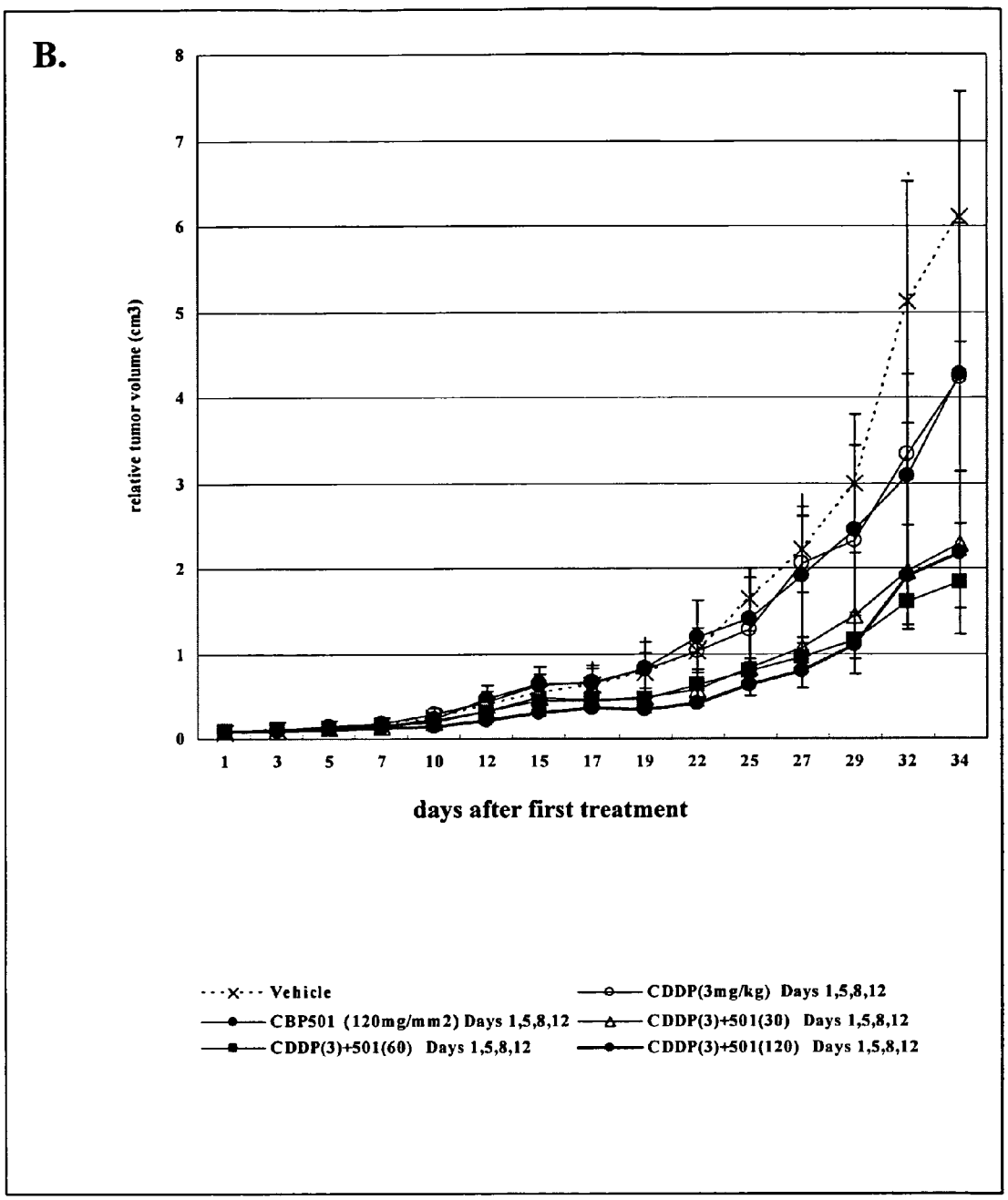

Established HCT-116 xenografts (0.2 cm$^3$) in SCID mice were treated two times each week for two weeks (i.e., on day 1, 5, 8, and 12) by intraperitoneal injection of the following: vehicle alone (DMSO); CBP501 (120 mg/m$^2$); cisplatin (CDDP, 3 mg/kg); a combination of CBP501 (30 mg/m$^2$) and cisplatin (CDDP, 3 mg/kg); a combination of CBP501 (60 mg/m$^2$) and cisplatin (CDDP, 3 mg/kg); or CBP501 (120 mg/m$^2$) and cisplatin (CDDP, 3 mg/kg). As shown in FIG. 3B, treatment with CBP501 alone or cisplatin (CDDP) alone, had little or no effect on tumor growth. However, a combination treatment of CBP and cisplatin (CDDP) caused significant inhibition of xenograft tumor growth. Interestingly, the effectiveness of the combination of CBP501 and cisplatin (CDDP) seemed unrelated to the concentration of CBP501: combination treatments using CBP501 at 30, 60, or 120 mg/m$^2$ had similar effectiveness. In contrast, CBP501 alone at the highest concentration tested, 120 mg/m$^2$, did not significantly inhibit xenograft tumor growth.

These results correlate with the prediction based on results from the in vitro sensitivity test using CBP501 and cisplatin (CDDP) as described above.

Various modifications can be made to the preferred embodiments without departing from the spirit and scope of the invention as defined in the appended claims.

What is claimed is:

1. A method for determining the sensitivity of a patient's cancerous cells to a candidate anti-cancer therapy, comprising:
   (a) exposing a sample of the patient's cancerous cells to the candidate anti-cancer therapy in vitro, wherein the candidate anti-cancer therapy comprises a G2 checkpoint-abrogating peptidomimetic selected from the group consisting of CBP500 (SEQ ID NO: 25), CBP501 (SEQ ID NO: 26), CBP504 (SEQ ID NO: 29), CBP505 (SEQ ID NO: 30), CBP506 (SEQ ID NO: 31), CBP510 (SEQ ID NO: 32), CBP511 (SEQ ID NO: 33), CBP512 (SEQ ID NO: 34), and CBP603 (SEQ ID NO: 37);
   (b) measuring the DNA content of each cancerous cell in the sample after exposure to the candidate anti-cancer therapy; and
   (c) determining the cell cycle distribution of the sample after exposure to the candidate anti-cancer therapy;
   wherein a change in the cell cycle distribution of the sample after exposure to the candidate anti-cancer therapy indicates sensitivity of the patient's cancerous cells to the therapy.

2. A method for determining the sensitivity of a patient's cancerous cells to a candidate anti-cancer therapy, comprising:
   (a) exposing a sample of the patient's cancerous cells to the candidate anti-cancer therapy in vitro, wherein the candidate anti-cancer therapy comprises a combination therapy comprising a DNA-damaging agent and a G2 checkpoint-abrogating agent, wherein the DNA-damaging agent is cisplatin (CDDP) and the G2 checkpoint-abrogating agent is CBP501 (SEQ ID NO: 26);
   (b) measuring the DNA content of each cancerous cell in the sample after exposure to the candidate anti-cancer therapy; and
   (c) determining the cell cycle distribution of the sample after exposure to the candidate anti-cancer therapy;
   wherein a change in the cell cycle distribution of the sample after exposure to the candidate anti-cancer therapy indicates sensitivity of the patient's cancerous cells to the therapy.

* * * * *

SEQUENCE LISTING

```
<160> NUMBER OF SEQ ID NOS: 49

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (12)..(12)
<223> OTHER INFORMATION: Xaa is Cyclohexyl-alanine
<220> FEATURE:
<221> NAME/KEY: SITE
<222> LOCATION: (13)..(13)
<223> OTHER INFORMATION: Xaa is Phenylalanine-2,3,4,5,6-F

<400> SEQUENCE: 4

Tyr Gly Arg Lys Lys Arg Arg Gln Arg Arg Arg Xaa Xaa Arg Ser
1               5                   10                  15

Pro Ser Tyr Tyr

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
```

```
<222> LOCATION: (12)..(12)
<223> OTHER INFORMATION: Xaa is Cyclohexyl-alanine
<220> FEATURE:
<221> NAME/KEY: SITE
<222> LOCATION: (13)..(13)
<223> OTHER INFORMATION: Xaa is Phenylalanine-2,3,4,5,6-F

<400> SEQUENCE: 5

Tyr Gly Arg Lys Lys Arg Arg Gln Arg Arg Xaa Xaa Arg Ser Pro
1               5                   10                  15

Ser Tyr

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (4)..(4)
<223> OTHER INFORMATION: Xaa is Cyclohexyl-alanine
<220> FEATURE:
<221> NAME/KEY: SITE
<222> LOCATION: (5)..(5)
<223> OTHER INFORMATION: Xaa is Phenylalanine-2,3,4,5,6-F

<400> SEQUENCE: 6

Arg Arg Arg Xaa Xaa Arg Ser Pro Ser Tyr Tyr
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (7)..(7)
<223> OTHER INFORMATION: Xaa is Cyclohexyl-alanine
<220> FEATURE:
<221> NAME/KEY: SITE
<222> LOCATION: (8)..(8)
<223> OTHER INFORMATION: Xaa is Phenylalanine-2,3,4,5,6-F

<400> SEQUENCE: 7

Arg Arg Gln Arg Arg Arg Xaa Xaa Arg Ser Pro Ser Tyr Tyr
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (7)..(7)
<223> OTHER INFORMATION: Xaa is Cyclohexyl-alanine
<220> FEATURE:
<221> NAME/KEY: SITE
<222> LOCATION: (8)..(8)
<223> OTHER INFORMATION: Xaa is Phenylalanine-2,3,4,5,6-F
<220> FEATURE:
<221> NAME/KEY: SITE
<222> LOCATION: (9)..(10)
<223> OTHER INFORMATION: Positions 9 to 10 are D-amino acids
```

```
<400> SEQUENCE: 8

Arg Arg Gln Arg Arg Xaa Xaa Ser Trp Pro Ser Tyr
1               5                   10

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (12)..(12)
<223> OTHER INFORMATION: Xaa is Cyclohexyl-alanine
<220> FEATURE:
<221> NAME/KEY: SITE
<222> LOCATION: (13)..(13)
<223> OTHER INFORMATION: Xaa is Phenylalanine-2,3,4,5,6-F
<220> FEATURE:
<221> NAME/KEY: SITE
<222> LOCATION: (14)..(14)
<223> OTHER INFORMATION: Xaa is aminoundecanoic acid

<400> SEQUENCE: 9

Tyr Gly Arg Lys Lys Arg Arg Gln Arg Arg Xaa Xaa Xaa Tyr Tyr
1               5                   10                  15

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(3)
<223> OTHER INFORMATION: Positions 1 to 3 are D-amino acids
<220> FEATURE:
<221> NAME/KEY: SITE
<222> LOCATION: (5)..(17)
<223> OTHER INFORMATION: Positions 5 to 17 are D-amino acids
<220> FEATURE:
<221> NAME/KEY: SITE
<222> LOCATION: (7)..(7)
<223> OTHER INFORMATION: Xaa is D-Phenylalanine-2,3,4,5,6-F
<220> FEATURE:
<221> NAME/KEY: SITE
<222> LOCATION: (8)..(8)
<223> OTHER INFORMATION: Xaa is D-Cyclohexyl-alanine
<220> FEATURE:
<221> NAME/KEY: SITE
<222> LOCATION: (19)..(19)
<223> OTHER INFORMATION: Position 19 is a D-amino acid

<400> SEQUENCE: 10

Tyr Tyr Ser Gly Ser Arg Xaa Xaa Arg Arg Arg Gln Arg Arg Lys Lys
1               5                   10                  15

Arg Gly Tyr

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(3)
<223> OTHER INFORMATION: Positions 1 to 3 are D-amino acids
```

```
<220> FEATURE:
<221> NAME/KEY: SITE
<222> LOCATION: (6)..(13)
<223> OTHER INFORMATION: Positions 6 to 13 are D-amino acids
<220> FEATURE:
<221> NAME/KEY: SITE
<222> LOCATION: (6)..(6)
<223> OTHER INFORMATION: Xaa is D-Phenylalanine-2,3,4,5,6-F
<220> FEATURE:
<221> NAME/KEY: SITE
<222> LOCATION: (7)..(7)
<223> OTHER INFORMATION: Xaa is D-Cyclohexyl-alanine

<400> SEQUENCE: 11

Tyr Ser Pro Trp Ser Xaa Xaa Arg Arg Arg Gln Arg Arg
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(2)
<223> OTHER INFORMATION: Positions 1 to 2 are D-amino acids
<220> FEATURE:
<221> NAME/KEY: SITE
<222> LOCATION: (6)..(13)
<223> OTHER INFORMATION: Positions 6 to 13 are D-amino acids
<220> FEATURE:
<221> NAME/KEY: SITE
<222> LOCATION: (6)..(6)
<223> OTHER INFORMATION: Xaa is D-Phenylalanine-2,3,4,5,6-F
<220> FEATURE:
<221> NAME/KEY: SITE
<222> LOCATION: (7)..(7)
<223> OTHER INFORMATION: Xaa is D-Cyclohexyl-alanine

<400> SEQUENCE: 12

Tyr Ser Pro Trp Ser Xaa Xaa Arg Arg Arg Gln Arg Arg
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(3)
<223> OTHER INFORMATION: Positions 1 to 3 are D-amino acids
<220> FEATURE:
<221> NAME/KEY: SITE
<222> LOCATION: (6)..(13)
<223> OTHER INFORMATION: Positions 6 to 13 are D-amino acids
<220> FEATURE:
<221> NAME/KEY: SITE
<222> LOCATION: (6)..(6)
<223> OTHER INFORMATION: Xaa is D-Phenylalanine-2,3,4,5,6-F

<400> SEQUENCE: 13

Tyr Ser Pro Trp Ser Xaa Pro Arg Arg Arg Gln Arg Arg
1               5                   10

<210> SEQ ID NO 14
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: SITE
<222> LOCATION: (1)..(2)
<223> OTHER INFORMATION: Positions 1 to 2 are D-amino acids
<220> FEATURE:
<221> NAME/KEY: SITE
<222> LOCATION: (6)..(6)
<223> OTHER INFORMATION: Xaa is D-Phenylalanine-2,3,4,5,6-F
<220> FEATURE:
<221> NAME/KEY: SITE
<222> LOCATION: (8)..(13)
<223> OTHER INFORMATION: Positions 8 to 13 are D-amino acids

<400> SEQUENCE: 14

Tyr Ser Pro Trp Ser Xaa Pro Arg Arg Arg Gln Arg Arg
1               5                   10

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (3)..(3)
<223> OTHER INFORMATION: Xaa is aminoundecanoic acid
<220> FEATURE:
<221> NAME/KEY: SITE
<222> LOCATION: (4)..(14)
<223> OTHER INFORMATION: Positions 4 to 14 are D-amino acids
<220> FEATURE:
<221> NAME/KEY: SITE
<222> LOCATION: (4)..(4)
<223> OTHER INFORMATION: Xaa is D-Phenylalanine-2,3,4,5,6-F
<220> FEATURE:
<221> NAME/KEY: SITE
<222> LOCATION: (5)..(5)
<223> OTHER INFORMATION: Xaa is D-Cyclohexyl-alanine
<220> FEATURE:
<221> NAME/KEY: SITE
<222> LOCATION: (16)..(16)
<223> OTHER INFORMATION: Position 16 is a D-amino acid

<400> SEQUENCE: 15

Tyr Tyr Xaa Xaa Xaa Arg Arg Arg Gln Arg Arg Lys Lys Arg Gly Tyr
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (2)..(2)
<223> OTHER INFORMATION: Xaa is aminoundecanoic acid
<220> FEATURE:
<221> NAME/KEY: SITE
<222> LOCATION: (3)..(13)
<223> OTHER INFORMATION: Positions 3 to 13 are D-amino acids
<220> FEATURE:
<221> NAME/KEY: SITE
<222> LOCATION: (3)..(3)
<223> OTHER INFORMATION: Xaa is D-Phenylalanine-2,3,4,5,6-F
<220> FEATURE:
<221> NAME/KEY: SITE
<222> LOCATION: (15)..(15)
<223> OTHER INFORMATION: Position 16 is a D-amino acid
```

<400> SEQUENCE: 16

Tyr Xaa Xaa Xaa Arg Arg Arg Gln Arg Arg Lys Lys Arg Gly Tyr
1               5                   10                  15

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (2)..(2)
<223> OTHER INFORMATION: Xaa is aminoundecanoic acid
<220> FEATURE:
<221> NAME/KEY: SITE
<222> LOCATION: (3)..(4)
<223> OTHER INFORMATION: Positions 3 to 4 are D-amino acids
<220> FEATURE:
<221> NAME/KEY: SITE
<222> LOCATION: (3)..(3)
<223> OTHER INFORMATION: Xaa is D-Phenylalanine-2,3,4,5,6-F

<400> SEQUENCE: 17

Tyr Xaa Xaa Xaa
1

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(1)
<223> OTHER INFORMATION: Xaa is aminoundecanoic acid
<220> FEATURE:
<221> NAME/KEY: SITE
<222> LOCATION: (2)..(11)
<223> OTHER INFORMATION: Positions 2 to 11 are D-amino acids
<220> FEATURE:
<221> NAME/KEY: SITE
<222> LOCATION: (2)..(2)
<223> OTHER INFORMATION: Xaa is D-Phenylalanine-2,3,4,5,6-F
<220> FEATURE:
<221> NAME/KEY: SITE
<222> LOCATION: (3)..(3)
<223> OTHER INFORMATION: Xaa is D-Cyclohexyl-alanine
<220> FEATURE:
<221> NAME/KEY: SITE
<222> LOCATION: (13)..(13)
<223> OTHER INFORMATION: Position 13 is a D-amino acid

<400> SEQUENCE: 18

Xaa Xaa Xaa Arg Arg Arg Gln Arg Arg Lys Lys Arg Gly Tyr
1               5                   10

<210> SEQ ID NO 19
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(1)
<223> OTHER INFORMATION: Xaa is aminoundecanoic acid
<220> FEATURE:
<221> NAME/KEY: SITE

```
<222> LOCATION: (2)..(3)
<223> OTHER INFORMATION: Positions 2 to 3 are D-amino acids
<220> FEATURE:
<221> NAME/KEY: SITE
<222> LOCATION: (2)..(2)
<223> OTHER INFORMATION: Xaa is D-Phenylalanine-2,3,4,5,6-F
<220> FEATURE:
<221> NAME/KEY: SITE
<222> LOCATION: (3)..(3)
<223> OTHER INFORMATION: Xaa is D-Cyclohexyl-alanine

<400> SEQUENCE: 19

Xaa Xaa Xaa
1

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(1)
<223> OTHER INFORMATION: Xaa is aminoundecanoic acid
<220> FEATURE:
<221> NAME/KEY: SITE
<222> LOCATION: (2)..(9)
<223> OTHER INFORMATION: Positions 2 to 9 are D-amino acids
<220> FEATURE:
<221> NAME/KEY: SITE
<222> LOCATION: (2)..(2)
<223> OTHER INFORMATION: Xaa is D-Phenylalanine-2,3,4,5,6-F
<220> FEATURE:
<221> NAME/KEY: SITE
<222> LOCATION: (3)..(3)
<223> OTHER INFORMATION: Xaa is D-Cyclohexyl-alanine

<400> SEQUENCE: 20

Xaa Xaa Xaa Arg Arg Arg Gln Arg Arg
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(1)
<223> OTHER INFORMATION: Xaa is 8-aminocaprylic acid
<220> FEATURE:
<221> NAME/KEY: SITE
<222> LOCATION: (2)..(9)
<223> OTHER INFORMATION: Positions 2 to 9 are D-amino acids
<220> FEATURE:
<221> NAME/KEY: SITE
<222> LOCATION: (2)..(2)
<223> OTHER INFORMATION: Xaa is D-Cyclohexyl-alanine
<220> FEATURE:
<221> NAME/KEY: SITE
<222> LOCATION: (3)..(3)
<223> OTHER INFORMATION: Xaa is D-Phenylalanine-2,3,4,5,6-F

<400> SEQUENCE: 21

Xaa Xaa Xaa Arg Arg Arg Gln Arg Arg
1               5

<210> SEQ ID NO 22
<211> LENGTH: 2
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(2)
<223> OTHER INFORMATION: Positions 1 to 2 are D-amino acids
<220> FEATURE:
<221> NAME/KEY: SITE
<222> LOCATION: (1)..(1)
<223> OTHER INFORMATION: Xaa is D-Phenylalanine-2,3,4,5,6-F
<220> FEATURE:
<221> NAME/KEY: SITE
<222> LOCATION: (2)..(2)
<223> OTHER INFORMATION: Xaa is D-Cyclohexyl-alanine

<400> SEQUENCE: 22

Xaa Xaa
1

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(8)
<223> OTHER INFORMATION: Positions 1 to 8 are D-amino acids
<220> FEATURE:
<221> NAME/KEY: SITE
<222> LOCATION: (1)..(1)
<223> OTHER INFORMATION: Xaa is D-Cyclohexyl-alanine
<220> FEATURE:
<221> NAME/KEY: SITE
<222> LOCATION: (2)..(2)
<223> OTHER INFORMATION: Xaa is D-Phenylalanine-2,3,4,5,6-F

<400> SEQUENCE: 23

Xaa Xaa Arg Arg Arg Gln Arg Arg
1               5

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: SITE
<222> LOCATION: (1)..(13)
<223> OTHER INFORMATION: Positions 1 to 13 are D-amino acids
<220> FEATURE:
<221> NAME/KEY: SITE
<222> LOCATION: (6)..(6)
<223> OTHER INFORMATION: Xaa is D-Phenylalanine-2,3,4,5,6-F
<220> FEATURE:
<221> NAME/KEY: SITE
<222> LOCATION: (7)..(7)
<223> OTHER INFORMATION: Xaa is D-Cyclohexyl-alanine

<400> SEQUENCE: 24

Tyr Ser Ser Trp Ser Xaa Xaa Arg Arg Arg Gln Arg Arg
1               5                   10

<210> SEQ ID NO 25
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: SITE
<222> LOCATION: (1)..(13)
<223> OTHER INFORMATION: Positions 1 to 13 are D-amino acids
<220> FEATURE:
<221> NAME/KEY: SITE
<222> LOCATION: (2)..(2)
<223> OTHER INFORMATION: Xaa is D-Benzoyl-phenylalanine
<220> FEATURE:
<221> NAME/KEY: SITE
<222> LOCATION: (6)..(6)
<223> OTHER INFORMATION: Xaa is D-Phenylalanine-2,3,4,5,6-F
<220> FEATURE:
<221> NAME/KEY: SITE
<222> LOCATION: (7)..(7)
<223> OTHER INFORMATION: Xaa is D-Cyclohexyl-alanine

<400> SEQUENCE: 25

Tyr Xaa Ser Trp Ser Xaa Xaa Arg Arg Arg Gln Arg Arg
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)..(1)
<223> OTHER INFORMATION: Xaa is D-Benzoyl-phenylalanine
<220> FEATURE:
<221> NAME/KEY: SITE
<222> LOCATION: (5)..(5)
<223> OTHER INFORMATION: Xaa is D-Phenylalanine-2,3,4,5,6-F
<220> FEATURE:
<221> NAME/KEY: SITE
<222> LOCATION: (6)..(6)
<223> OTHER INFORMATION: Xaa is D-Cyclohexyl-alanine

<400> SEQUENCE: 26

Xaa Ser Trp Ser Xaa Xaa Arg Arg Arg Gln Arg Arg
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(1)
<223> OTHER INFORMATION: Xaa is D-Benzoyl-phenylalanine
<220> FEATURE:
<221> NAME/KEY: SITE
<222> LOCATION: (2)..(2)
<223> OTHER INFORMATION: Xaa is 8-aminocaprylic acid
<220> FEATURE:
<221> NAME/KEY: SITE
<222> LOCATION: (3)..(10)
<223> OTHER INFORMATION: Positions 3 to 10 are D-amino acids
<220> FEATURE:
<221> NAME/KEY: SITE
<222> LOCATION: (3)..(3)
<223> OTHER INFORMATION: Xaa is D-Cyclohexyl-alanine
```

```
<220> FEATURE:
<221> NAME/KEY: SITE
<222> LOCATION: (4)..(4)
<223> OTHER INFORMATION: Xaa is D-Phenylalanine-2,3,4,5,6-F

<400> SEQUENCE: 27

Xaa Xaa Xaa Xaa Arg Arg Arg Gln Arg Arg
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(1)
<223> OTHER INFORMATION: Xaa is D-Benzoyl-phenylalanine
<220> FEATURE:
<221> NAME/KEY: SITE
<222> LOCATION: (2)..(2)
<223> OTHER INFORMATION: Xaa is 8-aminocaprylic acid
<220> FEATURE:
<221> NAME/KEY: SITE
<222> LOCATION: (3)..(10)
<223> OTHER INFORMATION: Positions 3 to 10 are D-amino acids
<220> FEATURE:
<221> NAME/KEY: SITE
<222> LOCATION: (3)..(3)
<223> OTHER INFORMATION: Xaa is D-Phenylalanine-2,3,4,5,6-F
<220> FEATURE:
<221> NAME/KEY: SITE
<222> LOCATION: (4)..(4)
<223> OTHER INFORMATION: Xaa is D-Cyclohexyl-alanine

<400> SEQUENCE: 28

Xaa Xaa Xaa Xaa Arg Arg Arg Gln Arg Arg
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(13)
<223> OTHER INFORMATION: Positions 1 to 13 are D-amino acids
<220> FEATURE:
<221> NAME/KEY: SITE
<222> LOCATION: (2)..(2)
<223> OTHER INFORMATION: Xaa is D-Benzoyl-phenylalanine
<220> FEATURE:
<221> NAME/KEY: SITE
<222> LOCATION: (6)..(6)
<223> OTHER INFORMATION: Xaa is D-Phenylalanine-2,3,4,5,6-F
<220> FEATURE:
<221> NAME/KEY: SITE
<222> LOCATION: (7)..(7)
<223> OTHER INFORMATION: Xaa is D-Cyclohexyl-alanine

<400> SEQUENCE: 29

Asp Xaa Ser Trp Ser Xaa Xaa Arg Arg Arg Gln Arg Arg
1               5                   10

<210> SEQ ID NO 30
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: SITE
<222> LOCATION: (1)..(13)
<223> OTHER INFORMATION: Positions 1 to 13 are D-amino acids
<220> FEATURE:
<221> NAME/KEY: SITE
<222> LOCATION: (1)..(1)
<223> OTHER INFORMATION: Xaa is D-Benzoylphenylalanine
<220> FEATURE:
<221> NAME/KEY: SITE
<222> LOCATION: (6)..(6)
<223> OTHER INFORMATION: Xaa is D-Phenylalanine-2,3,4,5,6-F
<220> FEATURE:
<221> NAME/KEY: SITE
<222> LOCATION: (7)..(7)
<223> OTHER INFORMATION: Xaa is D-Cyclohexyl-alanine

<400> SEQUENCE: 30

Xaa Asp Ser Trp Ser Xaa Xaa Arg Arg Arg Gln Arg Arg
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(13)
<223> OTHER INFORMATION: Positions 1 to 13 are D-amino acids
<220> FEATURE:
<221> NAME/KEY: SITE
<222> LOCATION: (1)..(1)
<223> OTHER INFORMATION: Xaa is D-Benzoyl-phenylalanine
<220> FEATURE:
<221> NAME/KEY: SITE
<222> LOCATION: (6)..(6)
<223> OTHER INFORMATION: Xaa is D-Phenylalanine-2,3,4,5,6-F
<220> FEATURE:
<221> NAME/KEY: SITE
<222> LOCATION: (7)..(7)
<223> OTHER INFORMATION: Xaa is D-Cyclohexyl-alanine

<400> SEQUENCE: 31

Xaa Ser Trp Ser Asp Xaa Xaa Arg Arg Arg Gln Arg Arg
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (7)..(7)
<223> OTHER INFORMATION: Xaa is D-Cyclohexyl-alanine
<220> FEATURE:
<221> NAME/KEY: SITE
<222> LOCATION: (8)..(8)
<223> OTHER INFORMATION: Xaa is D-Phenylalanine-2,3,4,5,6-F
<220> FEATURE:
<221> NAME/KEY: SITE
<222> LOCATION: (12)..(12)
<223> OTHER INFORMATION: Xaa is D-Benzoyl-phenylalanine
```

<400> SEQUENCE: 32

Arg Arg Arg Gln Arg Arg Xaa Xaa Ser Trp Ser Xaa
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (7)..(7)
<223> OTHER INFORMATION: Xaa is D-Benzoyl-phenylalanine
<220> FEATURE:
<221> NAME/KEY: SITE
<222> LOCATION: (11)..(11)
<223> OTHER INFORMATION: Xaa is D-Phenylalanine-2,3,4,5,6-F
<220> FEATURE:
<221> NAME/KEY: SITE
<222> LOCATION: (12)..(12)
<223> OTHER INFORMATION: Xaa is D-Cyclohexyl-alanine

<400> SEQUENCE: 33

Arg Arg Arg Gln Arg Arg Xaa Ser Trp Ser Xaa Xaa
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(12)
<223> OTHER INFORMATION: Positions 1 to 13 are D-amino acids
<220> FEATURE:
<221> NAME/KEY: SITE
<222> LOCATION: (7)..(7)
<223> OTHER INFORMATION: Xaa is D-Cyclohexyl-alanine
<220> FEATURE:
<221> NAME/KEY: SITE
<222> LOCATION: (8)..(8)
<223> OTHER INFORMATION: Xaa is D-Phenylalanine-2,3,4,5,6-F
<220> FEATURE:
<221> NAME/KEY: SITE
<222> LOCATION: (12)..(12)
<223> OTHER INFORMATION: Xaa is D-Benzoyl-phenylalanine

<400> SEQUENCE: 34

Arg Arg Arg Arg Arg Arg Xaa Xaa Ser Trp Ser Xaa
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(12)
<223> OTHER INFORMATION: Positions 1 to 13 are D-amino acids
<220> FEATURE:

```
<221> NAME/KEY: SITE
<222> LOCATION: (1)..(1)
<223> OTHER INFORMATION: Xaa is D-Benzoyl-phenylalanine
<220> FEATURE:
<221> NAME/KEY: SITE
<222> LOCATION: (5)..(5)
<223> OTHER INFORMATION: Xaa is D-Benzoyl-phenylalanine
<220> FEATURE:
<221> NAME/KEY: SITE
<222> LOCATION: (6)..(6)
<223> OTHER INFORMATION: Xaa is D-Cyclohexyl-alanine

<400> SEQUENCE: 35

Xaa Ser Trp Ser Xaa Xaa Arg Arg Arg Gln Arg Arg
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(1)
<223> OTHER INFORMATION: Xaa is D-Benzoyl-phenylalanine
<220> FEATURE:
<221> NAME/KEY: SITE
<222> LOCATION: (2)..(2)
<223> OTHER INFORMATION: Xaa is 8-aminocaprylic acid
<220> FEATURE:
<221> NAME/KEY: SITE
<222> LOCATION: (3)..(10)
<223> OTHER INFORMATION: Positions 3 to 10 are D-amino acids
<220> FEATURE:
<221> NAME/KEY: SITE
<222> LOCATION: (3)..(3)
<223> OTHER INFORMATION: Xaa is D-Benzoyl-phenylalanine
<220> FEATURE:
<221> NAME/KEY: SITE
<222> LOCATION: (4)..(4)
<223> OTHER INFORMATION: Xaa is D-Cyclohexyl-alanine

<400> SEQUENCE: 36

Xaa Xaa Xaa Xaa Arg Arg Arg Gln Arg Arg
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)..(1)
<223> OTHER INFORMATION: Xaa is D-Benzoyl-phenylalanine
<220> FEATURE:
<221> NAME/KEY: SITE
<222> LOCATION: (5)..(5)
<223> OTHER INFORMATION: Xaa is D-Phenylalanine-4NO2
<220> FEATURE:
<221> NAME/KEY: SITE
<222> LOCATION: (6)..(6)
<223> OTHER INFORMATION: Xaa is D-Cyclohexyl-alanine

<400> SEQUENCE: 37

Xaa Ser Trp Ser Xaa Xaa Arg Arg Arg Gln Arg Arg
```

```
1               5                  10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)..(1)
<223> OTHER INFORMATION: Xaa is D-Benzoyl-phenylalanine
<220> FEATURE:
<221> NAME/KEY: SITE
<222> LOCATION: (5)..(5)
<223> OTHER INFORMATION: Xaa is D-Phenylalanine-4NO2
<220> FEATURE:
<221> NAME/KEY: SITE
<222> LOCATION: (6)..(6)
<223> OTHER INFORMATION: Xaa is D-Cyclohexyl-alanine

<400> SEQUENCE: 38

Xaa Pro Trp Pro Xaa Xaa Arg Arg Arg Gln Arg Arg
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)..(1)
<223> OTHER INFORMATION: Xaa is D-Benzoyl-phenylalanine
<220> FEATURE:
<221> NAME/KEY: SITE
<222> LOCATION: (5)..(5)
<223> OTHER INFORMATION: Xaa is D-Phenylalanine-4NO2
<220> FEATURE:
<221> NAME/KEY: SITE
<222> LOCATION: (6)..(6)
<223> OTHER INFORMATION: Xaa is D-2-Naphthyl-alanyl

<400> SEQUENCE: 39

Xaa Pro Trp Pro Xaa Xaa Arg Arg Arg Gln Arg Arg
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)..(1)
<223> OTHER INFORMATION: Xaa is D-Phenylalanine-4NO2
<220> FEATURE:
```

```
<221> NAME/KEY: SITE
<222> LOCATION: (5)..(5)
<223> OTHER INFORMATION: Xaa is D-Phenylalanine-4NO2
<220> FEATURE:
<221> NAME/KEY: SITE
<222> LOCATION: (6)..(6)
<223> OTHER INFORMATION: Xaa is D-Cyclohexyl-alanine

<400> SEQUENCE: 40

Xaa Pro Trp Pro Xaa Xaa Arg Arg Arg Gln Arg Arg
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(11)
<223> OTHER INFORMATION: Positions 1 to 11 are D-amino acids
<220> FEATURE:
<221> NAME/KEY: SITE
<222> LOCATION: (1)..(1)
<223> OTHER INFORMATION: Xaa is D-Benzoyl-phenylalanine
<220> FEATURE:
<221> NAME/KEY: SITE
<222> LOCATION: (5)..(5)
<223> OTHER INFORMATION: Xaa is D-Phenylalanine-2,3,4,5,6-F
<220> FEATURE:
<221> NAME/KEY: SITE
<222> LOCATION: (6)..(6)
<223> OTHER INFORMATION: Xaa is D-Cyclohexyl-alanine

<400> SEQUENCE: 41

Xaa Ser Trp Ser Xaa Xaa Arg Arg Arg Arg Arg
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)..(1)
<223> OTHER INFORMATION: Xaa is D-Benzoyl-phenylalanine
<220> FEATURE:
<221> NAME/KEY: SITE
<222> LOCATION: (5)..(5)
<223> OTHER INFORMATION: Xaa is D-Phenylalanine-2,3,4,5,6-F
<220> FEATURE:
<221> NAME/KEY: SITE
<222> LOCATION: (6)..(6)
<223> OTHER INFORMATION: Xaa is D-Cyclohexyl-alanine

<400> SEQUENCE: 42

Xaa Ser Trp Ser Xaa Xaa Arg Arg Arg Arg Arg Arg
1               5                   10

<210> SEQ ID NO 43
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: SITE
<222> LOCATION: (1)..(12)
<223> OTHER INFORMATION: Positions 1 to 12 are D-amino acids
<220> FEATURE:
<221> NAME/KEY: SITE
<222> LOCATION: (1)..(1)
<223> OTHER INFORMATION: Xaa is D-Benzoyl-phenylalanine
<220> FEATURE:
<221> NAME/KEY: SITE
<222> LOCATION: (5)..(5)
<223> OTHER INFORMATION: Xaa is D-Phenylalanine-2,3,4,5,6-F
<220> FEATURE:
<221> NAME/KEY: SITE
<222> LOCATION: (6)..(6)
<223> OTHER INFORMATION: Xaa is D-Cyclohexyl-alanine

<400> SEQUENCE: 43

Xaa Ser Trp Ser Xaa Xaa Lys Lys Lys Lys Lys Lys
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(8)
<223> OTHER INFORMATION: Positions 1 to 8 are D-amino acids
<220> FEATURE:
<221> NAME/KEY: SITE
<222> LOCATION: (3)..(3)
<223> OTHER INFORMATION: Xaa is D-Benzoyl-phenylalanine
<220> FEATURE:
<221> NAME/KEY: SITE
<222> LOCATION: (7)..(7)
<223> OTHER INFORMATION: Xaa is D-Phenylalanine-2,3,4,5,6-F
<220> FEATURE:
<221> NAME/KEY: SITE
<222> LOCATION: (8)..(8)
<223> OTHER INFORMATION: Xaa is D-Cyclohexyl-alanine

<400> SEQUENCE: 44

Arg Arg Xaa Arg Arg Arg Xaa Xaa
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(9)
<223> OTHER INFORMATION: Positions 1 to 9 are D-amino acids
<220> FEATURE:
<221> NAME/KEY: SITE
<222> LOCATION: (8)..(8)
<223> OTHER INFORMATION: Xaa is D-Phenylalanine-2,3,4,5,6-F
<220> FEATURE:
<221> NAME/KEY: SITE
<222> LOCATION: (9)..(9)
<223> OTHER INFORMATION: Xaa is D-Cyclohexyl-alanine

<400> SEQUENCE: 45

Arg Arg Arg Xaa Arg Trp Arg Xaa Xaa
1               5
```

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(10)
<223> OTHER INFORMATION: Positions 1 to 10 are D-amino acids
<220> FEATURE:
<221> NAME/KEY: SITE
<222> LOCATION: (5)..(5)
<223> OTHER INFORMATION: Xaa is D-Benzoyl-phenylalanine
<220> FEATURE:
<221> NAME/KEY: SITE
<222> LOCATION: (9)..(9)
<223> OTHER INFORMATION: Xaa is D-Phenylalanine-2,3,4,5,6-F
<220> FEATURE:
<221> NAME/KEY: SITE
<222> LOCATION: (10)..(10)
<223> OTHER INFORMATION: Xaa is D-Cyclohexyl-alanine

<400> SEQUENCE: 46

Arg Arg Arg Arg Xaa Arg Trp Arg Xaa Xaa
1               5                   10

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(9)
<223> OTHER INFORMATION: Positions 1 to 9 are D-amino acids
<220> FEATURE:
<221> NAME/KEY: SITE
<222> LOCATION: (4)..(4)
<223> OTHER INFORMATION: Xaa is D-Benzoyl-phenylalanine
<220> FEATURE:
<221> NAME/KEY: SITE
<222> LOCATION: (8)..(8)
<223> OTHER INFORMATION: Xaa is D-Phenylalanine-2,3,4,5,6-F
<220> FEATURE:
<221> NAME/KEY: SITE
<222> LOCATION: (9)..(9)
<223> OTHER INFORMATION: Xaa is D-Cyclohexyl-alanine

<400> SEQUENCE: 47

Arg Arg Arg Xaa Arg Arg Arg Xaa Xaa
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(7)
<223> OTHER INFORMATION: Positions 1 to 7 are D-amino acids
<220> FEATURE:
<221> NAME/KEY: SITE
<222> LOCATION: (1)..(1)
<223> OTHER INFORMATION: Xaa is D-Benzoyl-phenylalanine
<220> FEATURE:
<221> NAME/KEY: SITE

```
-continued

<222> LOCATION: (5)..(5)
<223> OTHER INFORMATION: Xaa is D-Phenylalanine-2,3,4,5,6-F
<220> FEATURE:
<221> NAME/KEY: SITE
<222> LOCATION: (6)..(6)
<223> OTHER INFORMATION: Xaa is D-Cyclohexyl-alanine

<400> SEQUENCE: 48

Xaa Cys Trp Arg Xaa Xaa Cys
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(8)
<223> OTHER INFORMATION: Positions 1 to 8 are D-amino acids
<220> FEATURE:
<221> NAME/KEY: SITE
<222> LOCATION: (6)..(6)
<223> OTHER INFORMATION: Xaa is D-Phenylalanine-2,3,4,5,6-F
<220> FEATURE:
<221> NAME/KEY: SITE
<222> LOCATION: (7)..(7)
<223> OTHER INFORMATION: Xaa is D-Cyclohexyl-alanine

<400> SEQUENCE: 49

Tyr Cys Pro Trp Arg Xaa Xaa Cys
1               5
```